US011311707B2

(12) United States Patent
Follman et al.

(10) Patent No.: US 11,311,707 B2
(45) Date of Patent: Apr. 26, 2022

(54) ANTISEPTIC DELIVERY DEVICE AND METHOD OF USE

(71) Applicant: PROFESSIONAL DISPOSABLES INTERNATIONAL, INC., Orangeburg, NY (US)

(72) Inventors: Mark Follman, Glen Rock, NJ (US); Alan Bachman, Orange, CT (US); John Tanayan, Orangeburg, NY (US); Margarita Bastos, Plainsboro, NJ (US)

(73) Assignee: PROFESSIONAL DISPOSABLES INTERNATIONAL, INC., Orangeburg, NY (US)

( * ) Notice: Subject to any disclaimer, the term of this patent is extended or adjusted under 35 U.S.C. 154(b) by 355 days.

(21) Appl. No.: 16/323,872

(22) PCT Filed: Jul. 27, 2017

(86) PCT No.: PCT/US2017/044146
§ 371 (c)(1),
(2) Date: Feb. 7, 2019

(87) PCT Pub. No.: WO2018/031240
PCT Pub. Date: Feb. 15, 2018

(65) Prior Publication Data
US 2019/0209816 A1  Jul. 11, 2019

Related U.S. Application Data

(60) Provisional application No. 62/374,126, filed on Aug. 12, 2016, provisional application No. 62/431,012, filed on Dec. 7, 2016.

(51) Int. Cl.
*A61M 35/00* (2006.01)
*A61F 13/40* (2006.01)
(Continued)

(52) U.S. Cl.
CPC .................. *A61M 35/006* (2013.01)

(58) Field of Classification Search
CPC ........ A61M 35/00; A61M 1/00; A61M 27/00; A61M 1/962; A61M 1/80;
(Continued)

(56) References Cited

U.S. PATENT DOCUMENTS 6,729,786 B1   5/2004  Tufts et al.
7,097,629 B2   8/2006  Blair
(Continued)

FOREIGN PATENT DOCUMENTS

EP   1 549 381 B1   7/2005
EP   1549381   *   3/2010
(Continued)

OTHER PUBLICATIONS

International Search Report dated Nov. 2, 2017 in International Application No. PCT/US2017/044146.
(Continued)

*Primary Examiner* — Tatyana Zalukaeva
*Assistant Examiner* — Ilya Y Treyger
(74) *Attorney, Agent, or Firm* — Baker Botts L.L.P.

(57) ABSTRACT

A fluid delivery device (100) comprising a housing (200) having a proximal end, a distal end, and a length therebetween, an activation device (300) disposed within the housing (200), a bottle (400) at least partially receivable in the proximal end of the housing (200), the bottle (400) containing a fluid medium therein and sealed by a laminate seal element, wherein the laminate seal element is proximate the activation device (300) and disposed a predetermined distance dimension therefrom, and a foam pad (500) coupled to a distal end of the housing (200), wherein the bottle (400) is axially movable with respect to the housing (200) at least the predetermined distance dimension to engage the laminate
(Continued)

seal element with the activation device (300) to dispense the fluid medium from the bottle (400) through the foam pad. A method of using such a delivery device is provided.

17 Claims, 23 Drawing Sheets

(51) Int. Cl.
*A61M 1/00* (2006.01)
*A61M 27/00* (2006.01)
*A61F 13/00* (2006.01)

(58) Field of Classification Search
CPC ... A61M 2202/095; A61F 13/00; A61F 13/02; A61F 13/00068; A61F 13/0203; A61F 2013/00174
See application file for complete search history.

(56) References Cited

U.S. PATENT DOCUMENTS

| | | | |
|---|---|---|---|
| 7,261,701 B2 | 8/2007 | Davis et al. | |
| 7,540,681 B2 | 6/2009 | Cybulski et al. | |
| 7,824,122 B2 | 11/2010 | Flores et al. | |
| 8,348,537 B2 | 1/2013 | Cable, Jr. et al. | |
| 8,556,529 B2 | 10/2013 | Law et al. | |
| 8,801,312 B2 | 8/2014 | Guzman et al. | |
| 8,911,771 B2 | 12/2014 | Vanek et al. | |
| 9,345,868 B2 | 5/2016 | Frith | |
| 2006/0115520 A1 | 6/2006 | Vanek et al. | |
| 2008/0267689 A1 | 10/2008 | Soller et al. | |
| 2010/0168638 A1 | 7/2010 | Korogi et al. | |
| 2011/0147260 A1 | 6/2011 | Perchtold et al. | |
| 2012/0219347 A1 | 8/2012 | Law et al. | |
| 2013/0123717 A1 | 5/2013 | Cable, Jr. et al. | |
| 2013/0251439 A1 | 9/2013 | Guzman | |
| 2013/0287471 A1 | 10/2013 | Boone et al. | |
| 2014/0081221 A1 | 3/2014 | McDonald et al. | |
| 2014/0081222 A1 | 3/2014 | McDonald et al. | |
| 2015/0297876 A1 | 10/2015 | Lockwood et al. | |
| 2016/0166816 A1 | 6/2016 | Mingione et al. | |
| 2018/0161559 A1 | 6/2018 | Sei et al. | |

FOREIGN PATENT DOCUMENTS

| | | | | |
|---|---|---|---|---|
| WO | WO2009076612 | * | 12/2008 | |
| WO | WO 2009/076612 A1 | | 6/2009 | |
| WO | WO 2014/195767 | * | 9/2013 | |
| WO | WO 2014/195767 A1 | | 12/2014 | |
| WO | WO-2014195767 A1 | * | 12/2014 | .......... A61M 5/1782 |
| WO | WO2016102429 | * | 12/2015 | |
| WO | WO 2016/102429 A1 | | 6/2016 | |

OTHER PUBLICATIONS

U.S. Appl. No. 15/981,502 (US 2018/0333566), filed May 16, 2018 (filed Nov. 22, 2018).
U.S. Appl. No. 15/981,502, dated Jul. 2, 2021 Notice of Allowance.

* cited by examiner

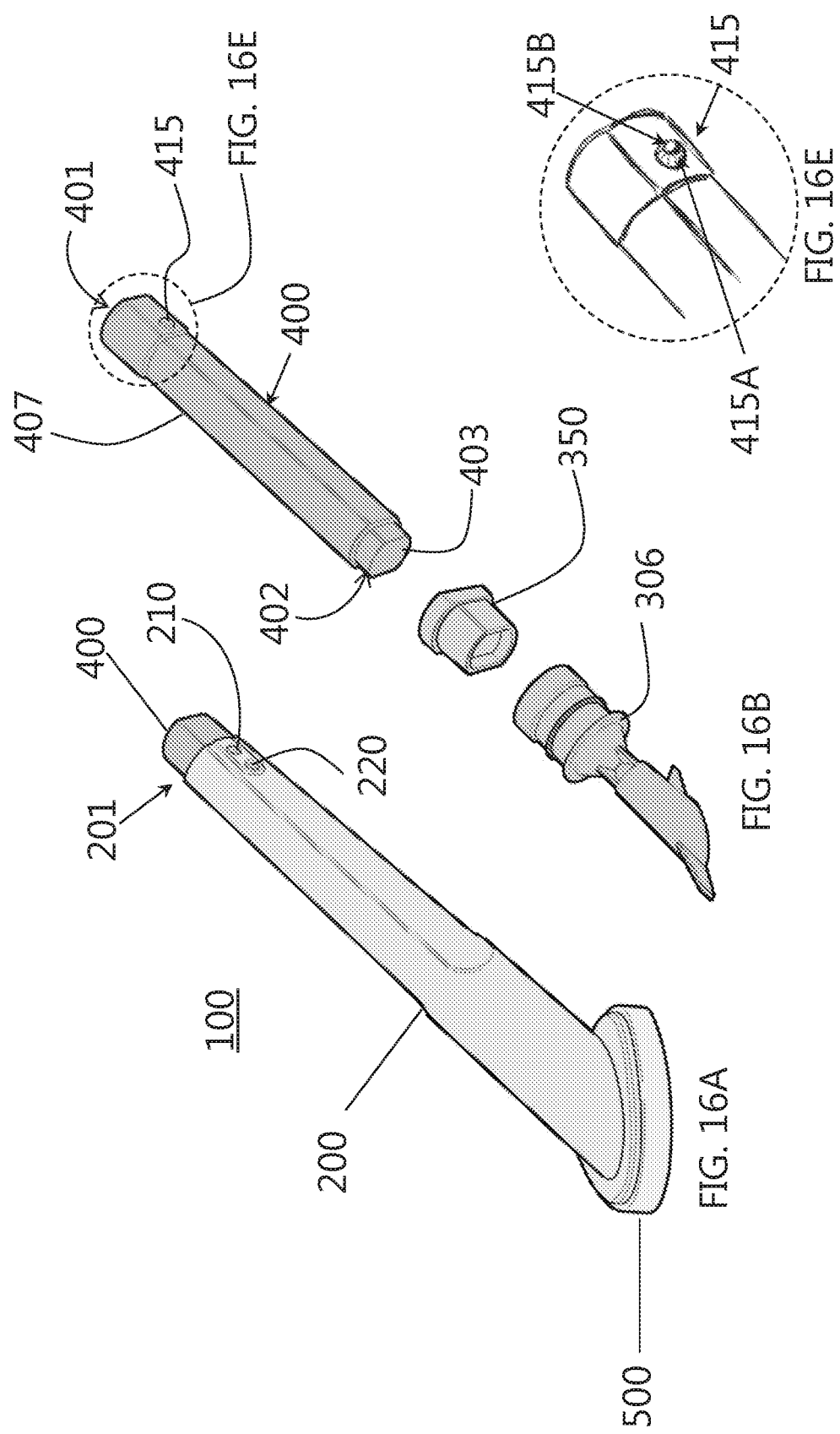

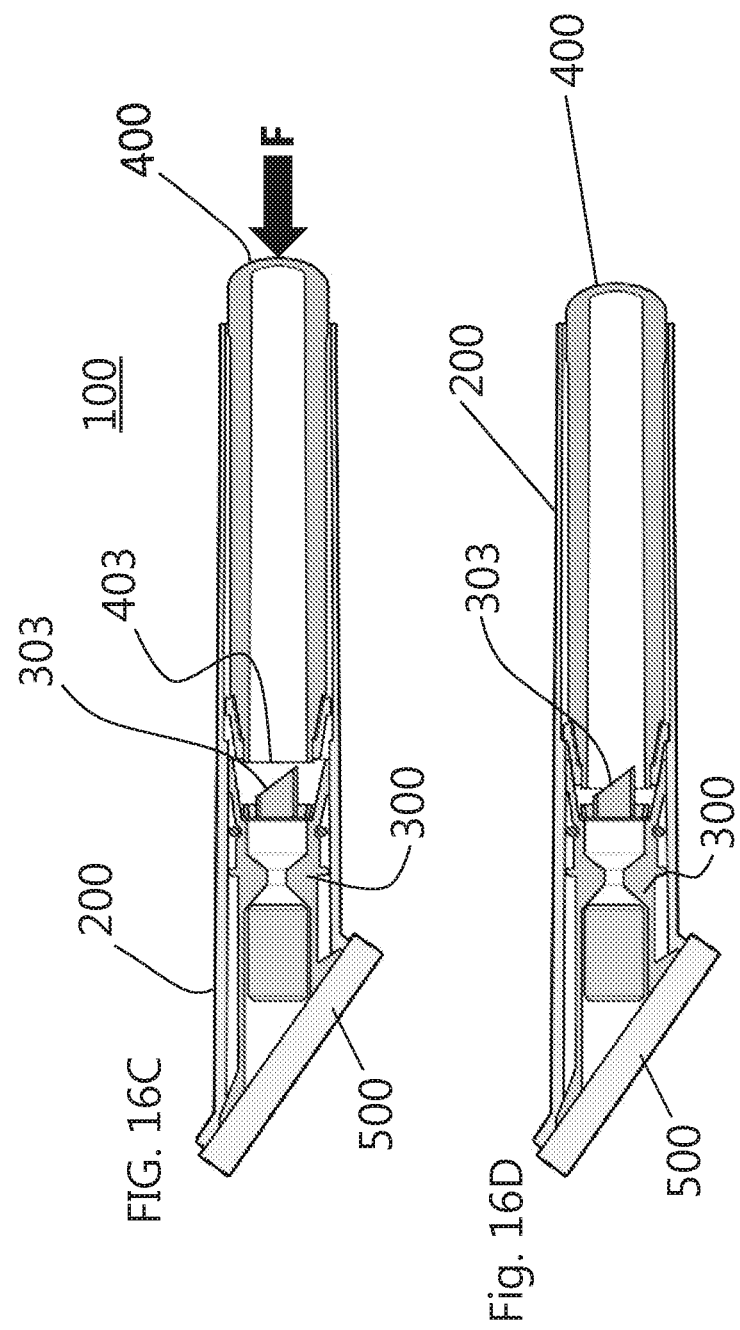

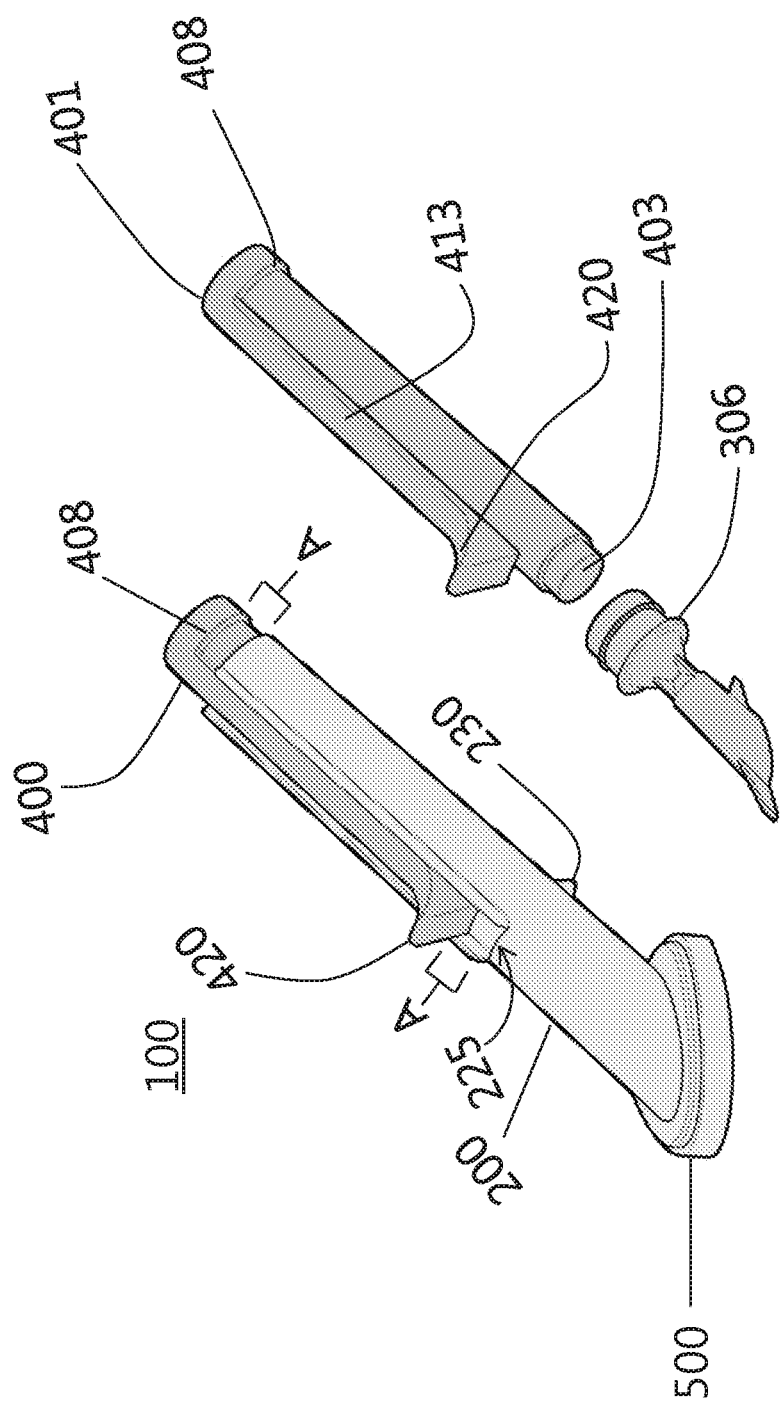

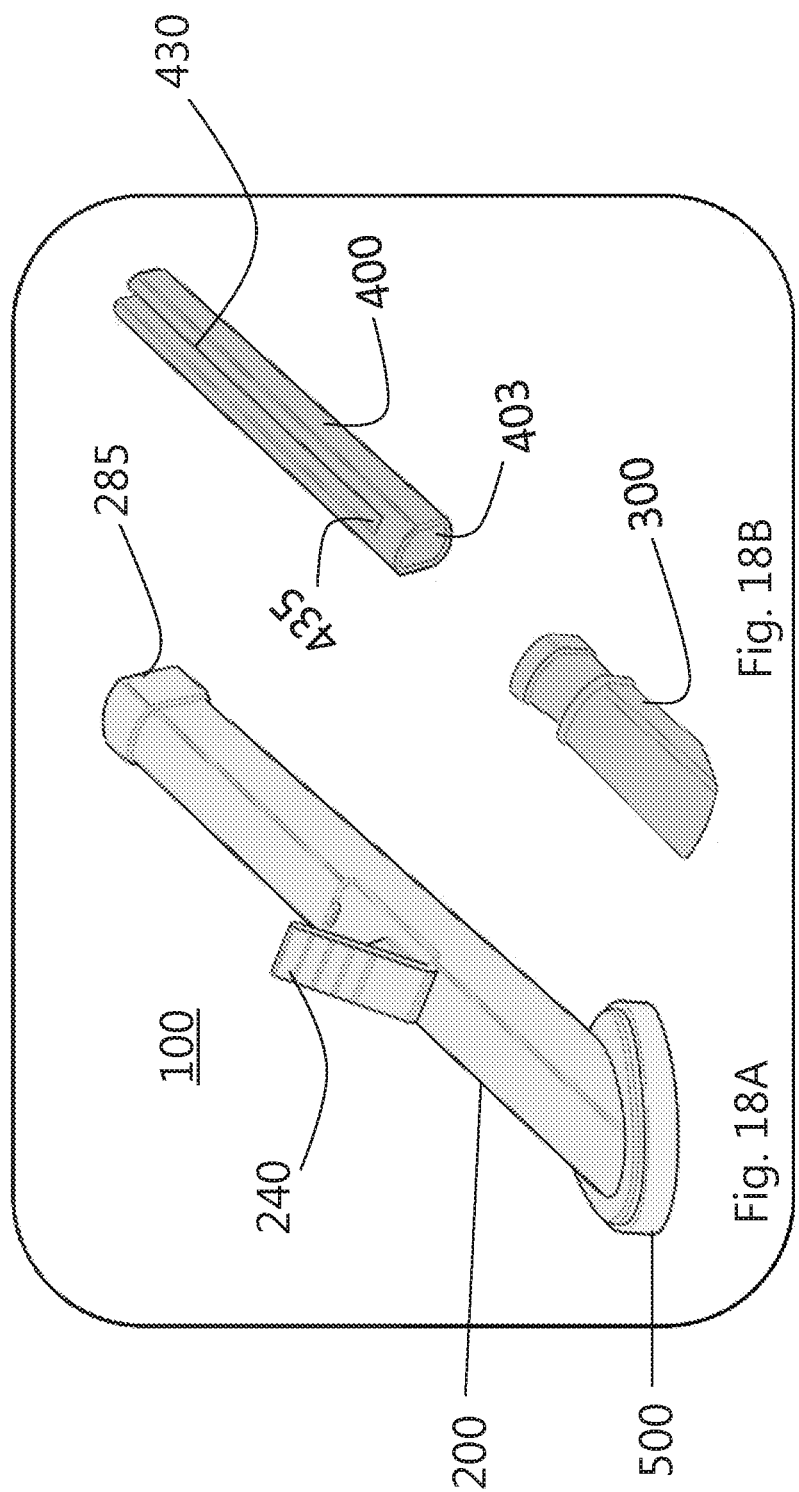

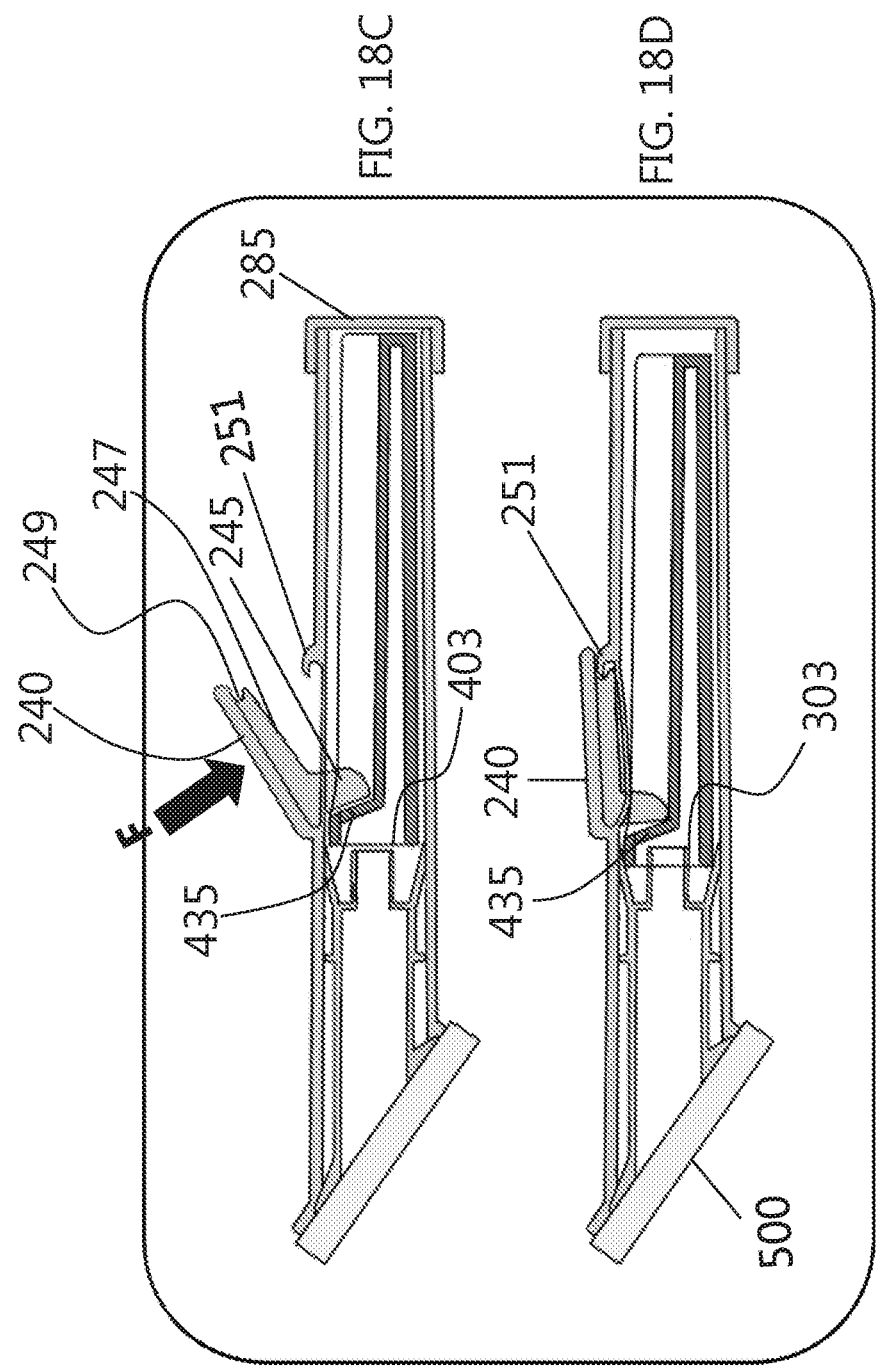

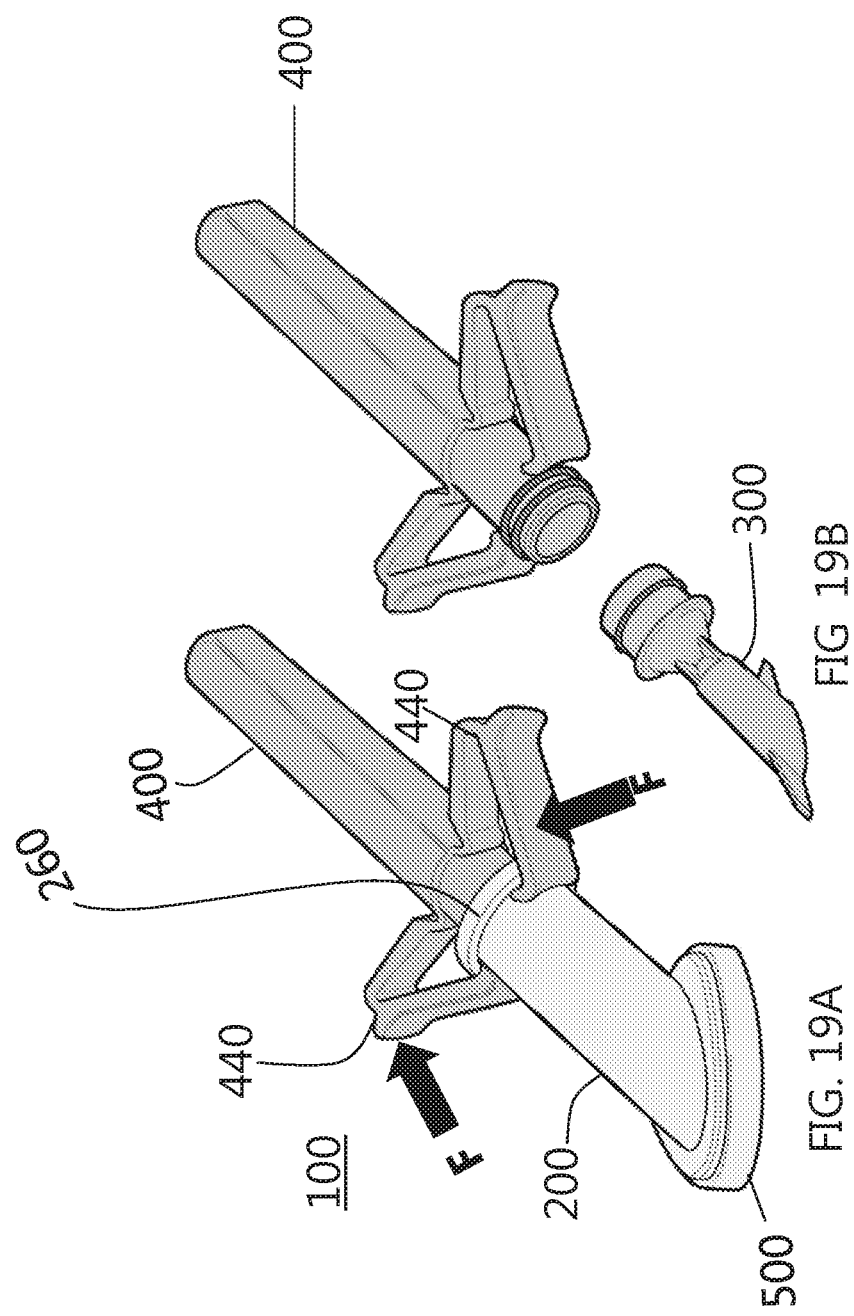

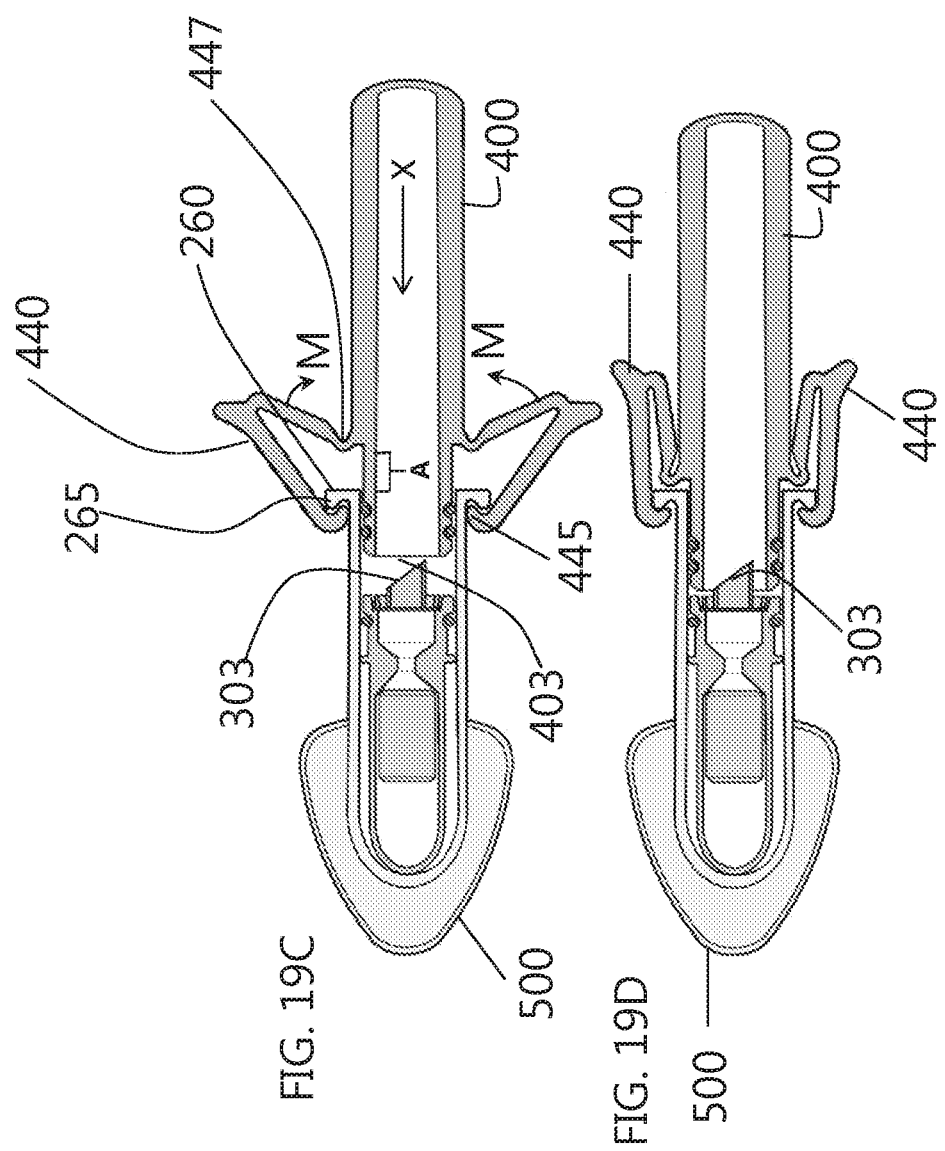

ANTISEPTIC DELIVERY DEVICE AND METHOD OF USE

CROSS-REFERENCE TO RELATED APPLICATIONS

This application is a U.S. National Stage Patent Application under 35 U.S.C. § 371 of International Application No. PCT/US2017/044146, filed on Jul. 27, 2017, which claims priority to U.S. Provisional Application Ser. No. 62/374,126, filed Aug. 12, 2016 and U.S. Provisional Application Ser. No. 62/431,012, filed Dec. 7, 2016 the contents of each of which are hereby incorporated by reference in their entirety.

BACKGROUND OF THE DISCLOSED SUBJECT MATTER

Field of the Disclosed Subject Matter

The disclosed subject matter relates to an antiseptic delivery device and method of use.

Description of the Related Art

It is common practice to prepare a patient for surgery by applying a fluid, such as an antiseptic solution, to the target body portion. As such, a number of devices and methods exist for dispensing and applying a fluid, i.e., an antiseptic, to the skin of a patient. A problem with some typical conventional fluid delivery devices is the inclusion of an ampoule that needs to be broken in order to release its fluid contents, which brings about risks such as occlusion of the device and loose glass contacting the patient's skin.

To overcome at least such problems, fluid delivery devices have been designed that use components having sealable membranes rather than ampoules. One drawback of such devices is that they tend to employ complex levers or push button actuation, each of which requires a high degree of user effort and exertion of high activation forces and can require two hands to operate such devices. Such force is not optimal for the physical capabilities of all user group populations and such devices can be cumbersome. Such devices are not ergonomically designed for the end user, as such designs induce extensive stress or fatigue upon the end user during system activation.

Thus, there remains a continued need for an improved fluid delivery device and method of use. The presently disclosed subject matter satisfies these and other needs. Embodiments of the disclosed subject matter provide a device and method of use that utilizes a device that can release a fluid medium, such as an antiseptic, onto the skin of a patient. Further, the device and method require a low degree of activation force due to the employment of unique rotational and/or axial movement systems, and is thereby optimal for the physical capabilities of all target user group populations and ergonomically designed for the end user. Finally, the disclosed subject matter is readily adaptable to be designed to accommodate any desired volume of fluid for delivery, and is designed to provide any desired tint color/concentration to the fluid being delivered.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a fluid delivery device. The fluid delivery device comprises a housing having a proximal end, a distal end, and a length therebetween, an activation device disposed within the housing, a bottle at least partially receivable in the proximal end of the housing, the bottle containing a fluid medium therein and sealed by a laminate seal element, wherein the laminate seal element is proximate the activation device and disposed a predetermined distance dimension therefrom, and a foam pad coupled to a distal end of the housing, wherein the bottle is axially movable with respect to the housing at least the predetermined distance dimension to engage the laminate seal element with the activation device to dispense the fluid medium from the bottle to the foam pad.

In accordance with another aspect of the disclosed subject matter, a method of using a fluid delivery device is provided, comprising providing a fluid delivery device including a housing having a proximal end, a distal end, and a length therebetween, an activation device disposed within the housing, a bottle at least partially receivable in the proximal end of the housing, the bottle containing a fluid medium therein and sealed by a laminate seal element, wherein the laminate seal element is proximate the activation device and disposed a predetermined distance dimension therefrom, and a foam pad coupled to a distal end of the housing. The method further includes rotating the bottle within the housing to axially move the laminate seal element at least the predetermined distance dimension with respect to the housing, and engaging the laminate seal element with the activation device to dispense the fluid medium from the bottle to the foam pad.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 16A is a perspective view of a fluid delivery device in an initial position, according another embodiment of the disclosed subject matter.

FIG. 16B is an exploded view of the bottle and activation device of the fluid delivery device of FIG. 16A.

FIG. 16C is a side cross-sectional view of the fluid delivery device of FIG. 16A in the initial position.

FIG. 16D is a side cross-sectional view of the fluid delivery device of FIG. 16C in the final position.

FIG. 16E is a detail view of the detent of FIG. 16B.

FIG. 17A is a perspective view of a fluid delivery device in an initial position, according another embodiment of the disclosed subject matter.

FIG. 17B is an exploded view of the bottle and activation device of the fluid delivery device of FIG. 17A.

FIG. 18A is a perspective view of a fluid delivery device in an initial position, according another embodiment of the disclosed subject matter.

FIG. 18B is an exploded view of the bottle and activation device of the fluid delivery device of FIG. 18A.

FIG. 18C is a side cross-sectional view of the fluid delivery device of FIG. 18A in the initial position.

FIG. 18D is a side cross-sectional view of the fluid delivery device of FIG. 18C in the final position.

FIG. 19A is a perspective view of a fluid delivery device in an initial position, according another embodiment of the disclosed subject matter.

FIG. 19B is an exploded view of the bottle and activation device of the fluid delivery device of FIG. 19A.

FIG. 19C is a top cross-sectional view of the fluid delivery device of FIG. 19A in the initial position.

FIG. 19D is a top cross-sectional view of the fluid delivery device of FIG. 19C in the final position.

DETAILED DESCRIPTION

Reference will now be made in detail to embodiments of the disclosed subject matter, an example of which is illustrated in the accompanying drawings. The disclosed subject matter will be described in conjunction with the detailed description of the system.

In accordance with the disclosed subject matter, a fluid delivery device is provided. The fluid delivery device includes a housing having a proximal end, a distal end, and a length therebetween, and an activation device disposed within the housing. The device further includes a bottle at least partially receivable in the proximal end of the housing, the bottle containing a fluid medium therein and sealed by a laminate seal element, wherein the laminate seal element is proximate the activation device and disposed a predetermined distance dimension therefrom, and a foam pad coupled to a distal end of the housing. The bottle is axially movable with respect to the housing at least the predetermined distance dimension to engage the laminate seal element with the activation device, and to dispense the fluid medium from the bottle to the foam pad.

A method of using the fluid delivery device described above is also disclosed. The details of the method of using the device will be described in detail in conjunction with the features of the fluid delivery device.

Figure 1:
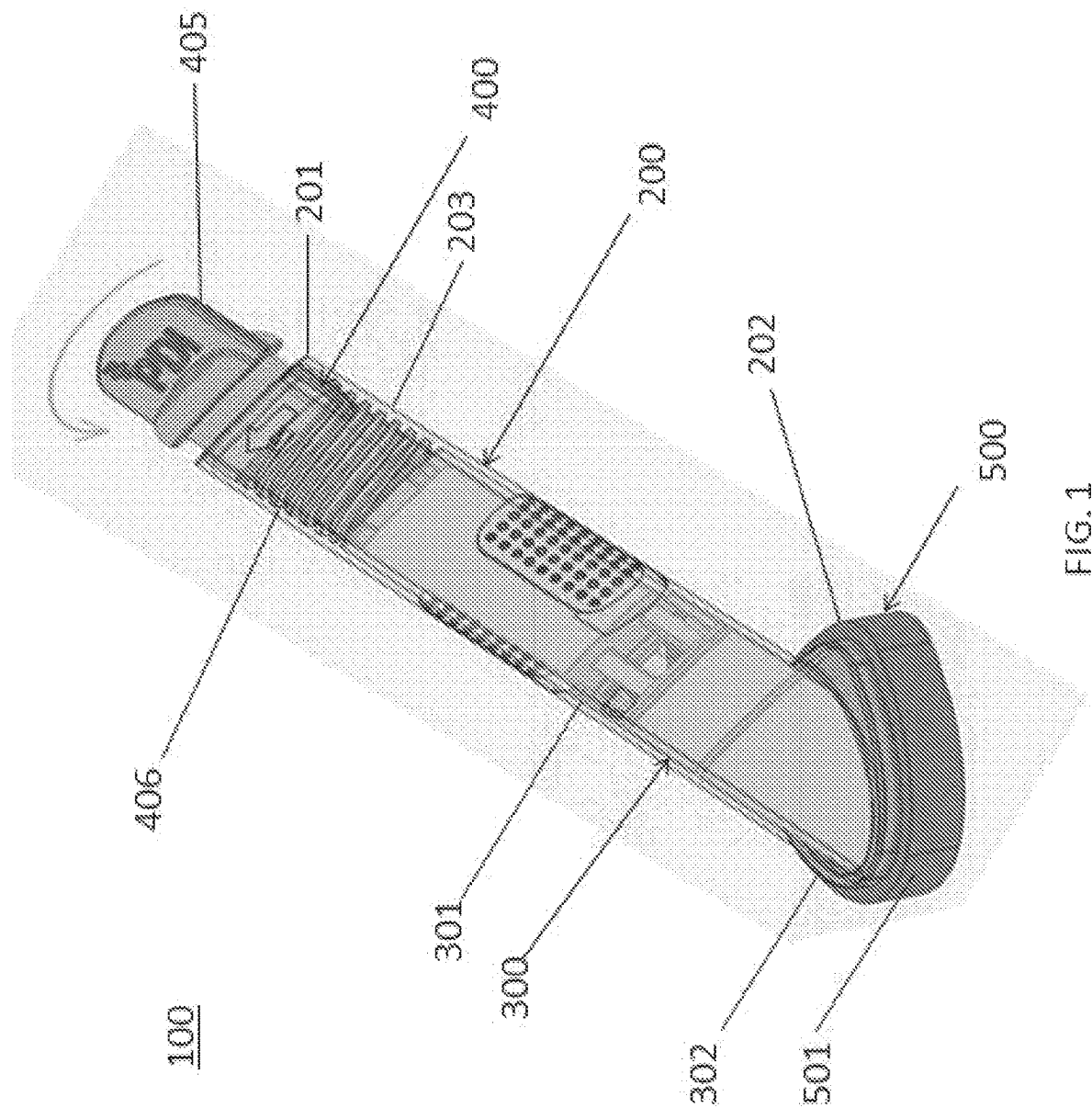
FIG. 1 is a perspective view of a fluid delivery device in an initial position, according to the disclosed subject matter.
Figure 2:
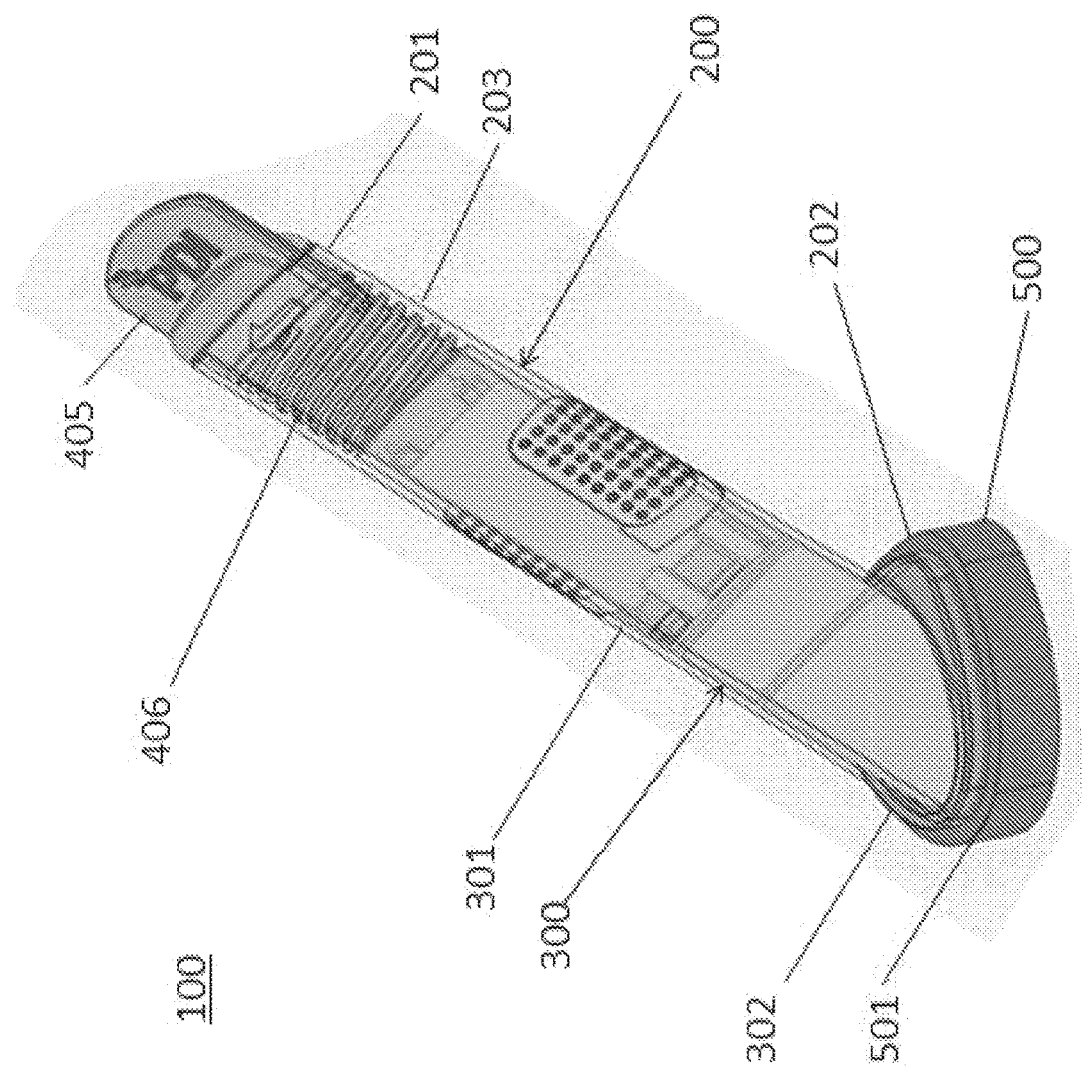
FIG. 2 is a perspective view of the fluid delivery device of FIG. 1 in a final position, according to the disclosed subject matter.

Solely for purpose of illustration, an embodiment of a fluid delivery device 100 and method of use, is shown schematically in FIG. 1. The examples herein are not intended to limit the scope of the disclosed subject matter in any manner. Particularly, and as illustrated, the fluid delivery device 100 of FIG. 1 includes a housing 200, an activation device 300, a bottle 400 containing a fluid medium therein, and a pad, such as a foam pad 500. The bottle 400 is at least partially received within the housing 200 and is axially movable between an initial position and a final position. FIG. 1 depicts the bottle in the initial position and FIG. 2 depicts the delivery device in the final position, as further described herein. A proximal end of the fluid delivery device is closest to a user handling the device, whereas a distal end of the fluid delivery device at the foam pad is to be engaged with an individual, such as a patient.

Figure 3:
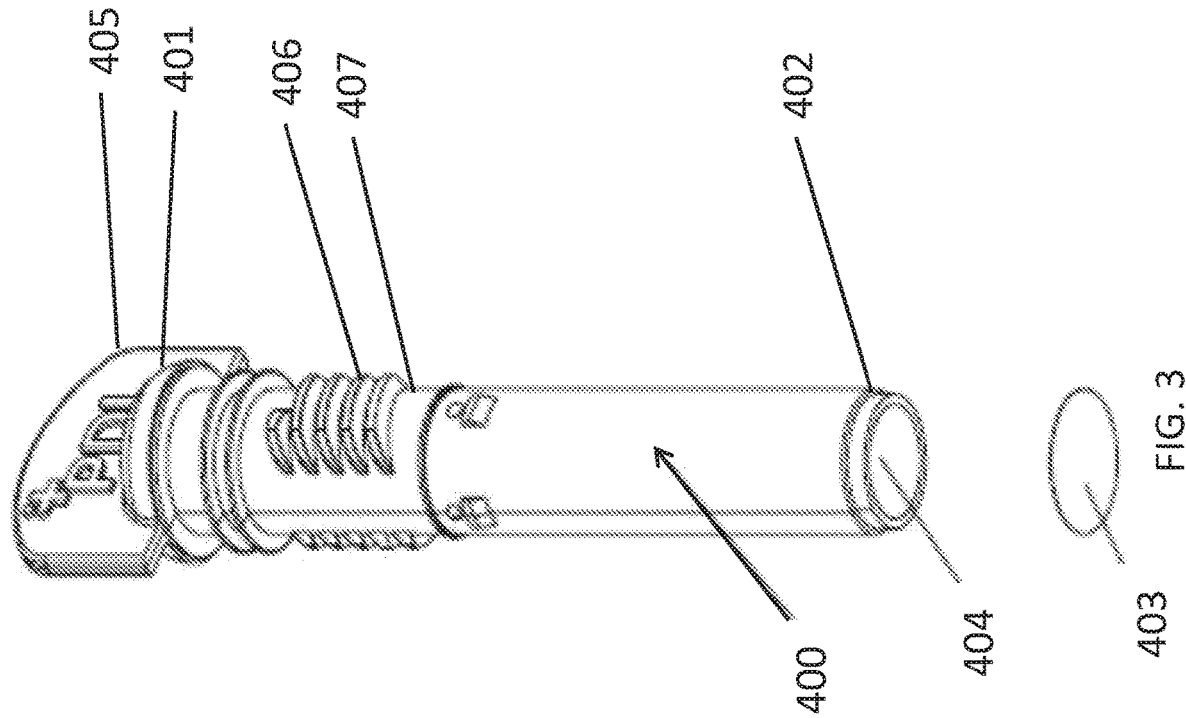
FIG. 3 is an exploded view of the bottle assembly of the fluid delivery device of FIG. 1, according to the disclosed subject matter.

FIG. 3 depicts an exploded view of a sub-assembly of the fluid delivery device 100 of FIG. 1, specifically, the bottle 400 and laminate seal element 403. As embodied herein, and as depicted in FIG. 3, the bottle 400 can include a proximal end 401 and a distal end 402, and can contain a fluid medium therein. The proximal end 401 can define a closed end. In contrast, the distal end 402 of the bottle 400 can define an aperture 404 which can be sealed, as later discussed herein. The bottle 400 can have any suitable shape and is depicted as tubular in FIG. 3. However, other bottle shapes that complement the housing are contemplated herewith.

As shown in FIG. 3, the bottle 400 can further include exterior threads 406 along an exterior surface and sidewall 407 of the bottle 400. The exterior threads 406 can be disposed on along a portion of the sidewall 407 of the bottle 400 proximate the proximal end 401 of the bottle 400, as depicted in FIG. 3. Alternatively, the exterior threads 406 can be disposed about other portions along the sidewall 407 of the bottle 400, including along the longitudinal length of the bottle 400. For example, and not limitation, the bottle 400 and the exterior threads 406 can be integrally formed from the same material. As discussed below, the exterior threads 406 of the bottle 400 can be a predetermined size and pitch to engage interior threads 203 of the housing 200 and facilitate axial movement of the bottle 400 with respect to the housing 200, as further described herein.

As embodied herein, the exterior threads 406 can be circumferentially disposed along the exterior surface and sidewall 407 of the bottle 400. Alternatively, the exterior threads 406 can be partially circumferentially disposed along the exterior surface and sidewall 407 of the bottle 400, as shown in FIG. 3. The exterior threads 406 can include a bead projection, or alternatively can define a flange with top and bottom surfaces, as shown in FIG. 3. In addition to facilitating axial movement of the bottle 400 with respect to the housing 200, the exterior threads 406 can also aid in stabilizing the bottle 400 within the housing 200. The exterior threads 406 can thereby prevent transverse movement of the bottle 400 with respect to the housing 200.

Figure 4:
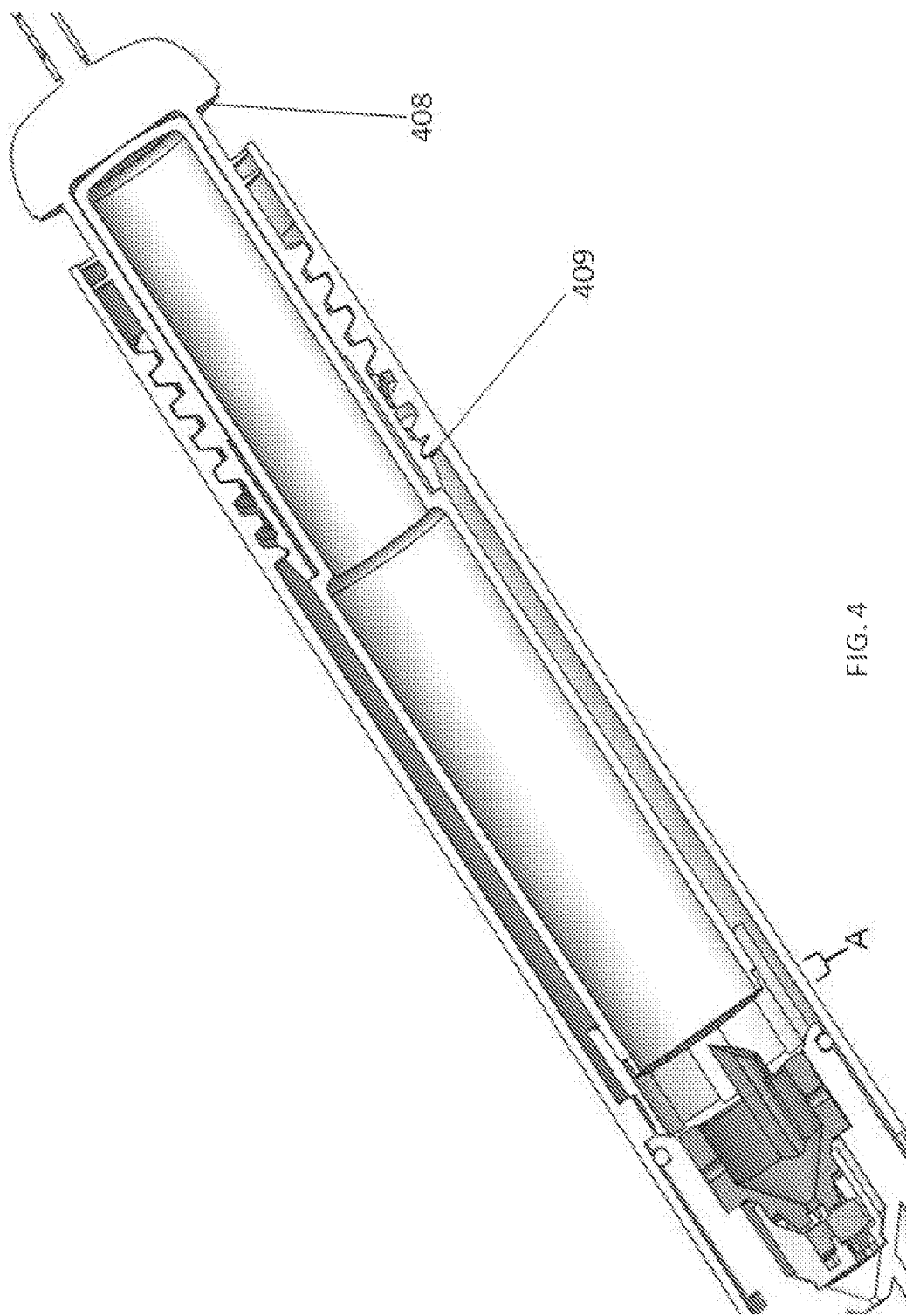
FIG. 4 is an enlarged cross sectional perspective view of an embodiment of the fluid delivery device of FIG. 1.
Figure 5:
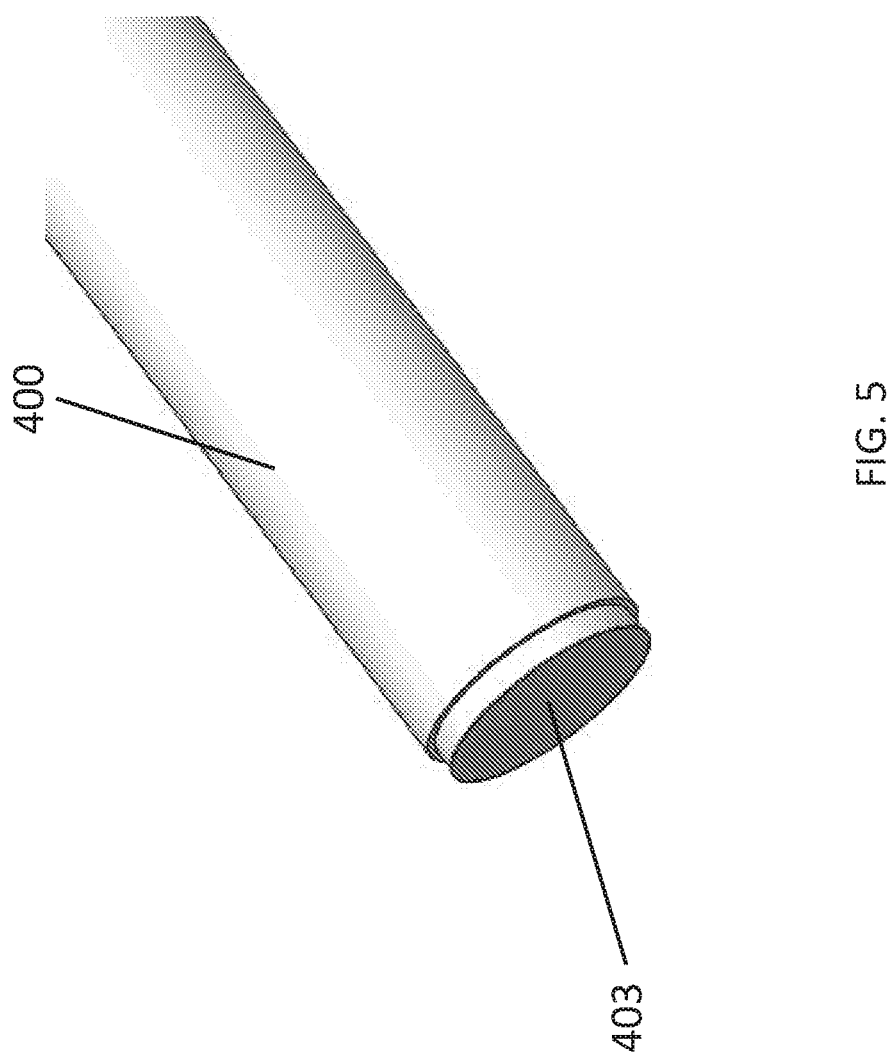
FIG. 5 is an enlarged perspective view of an alternate embodiment of the bottle seal assembly of the fluid delivery device, according to the disclosed subject matter.

As shown in FIG. 4, the proximal end of the bottle 400 can further define a stop member 408. The stop member 408 can be a circumferential ring such that the stop member 408 prevents further axial movement of the bottle 400 within the housing 200, as further discussed here. However, all shapes of stop members suitable to prevent axial movement of the bottle 400 with respect to the housing 200 are contemplated herein. For example, the stop member 408 can be a single planar flange extending radially outward from the proximal end 401 of the bottle 400 (not shown), as discussed herein with respect to FIGS. 17A-17D. The bottle 400 can further have a lock member 409 that prevents rotation of the bottle 400 in a counter direction after the bottle 400 has moved an axial distance with respect to the housing 200. The lock member 409 thereby can prevent premature or undesirable movement or rotation of the bottle 400. The axial distance the bottle moves with respect to the housing includes the predetermined distance dimension A as discussed further herein.

As embodied herein, and returning to FIG. 3, the bottle 400 can further include a handle 405. The bottle 400 can be rotatable by rotational movement of the handle 405, which in turn, and as discussed in further detail below, can axially move the bottle 400 with respect to the housing 200 in a direction toward the pad 500. In some embodiments, and as depicted in FIG. 3, the handle 405 can be a flange. However, all shapes of handles suitable to facilitate rotation of a bottle 400 are contemplated herein. For example, the handle 405 can be of a configuration that allows the user to both grip and rotate the bottle with the same hand at the same time. Such a handle 405 configuration providing one-handed rotational movement of the bottle 400 can be a loop or a structure capable of being reached and moved by a single finger of a user's hand while the user also maintains grip of the bottle 400 (not shown). The handle 405 can be coupled to the proximal end 401 of the bottle 400. For example, and not limitation, the handle 405 and the bottle 400 can also be integrally formed of the same material to form a monolithic structure. Additionally, the handle 405 can define the stop member 408. Other embodiments further disclose one-handed operation as further disclosed below with respect to FIGS. 16A-19D.

Depending on the size of the bottle 400, the volume of the bottle can vary. For example and not limitation, the bottle can contain at least 5 mL of fluid medium to enable the device to accommodate a treatment area for one applicator as approximately up to 7 inches by 7 inches (18 cm by 18 cm). In larger embodiments, and for the purpose of example, the bottle can contain at least 10.5 mL of fluid medium therein to enable the device to accommodate a treatment area for one applicator as approximately up to 10.25 inches by 10.25 inches (26 cm by 26 cm). In other embodiments, the bottle can contain at least 26 mL of fluid medium therein to enable the device to accommodate a treatment area for one applicator as approximately up to 16 inches by 16 inches (41 cm by 41 cm). The bottle 400 may have any thickness suitable to hold fluid contents therein, such as for example and not limitation, about 0.09 inches to about 0.12 inches (0.23 cm to 0.31 cm) Additionally, the distal end 402 of the bottle 400 may provide a surface for engagement of a laminate seal element 403, as further discussed herein.

The bottle 400 can further comprise a laminate seal element 403, wherein the laminate seal element 403 can be disposed at the distal end 402. The laminate seal element 403 can engage with the distal end 402 of the bottle 400 to form a fluid-tight, hermetic seal. In one embodiment, the outer perimeter surface area of the laminate seal element 403 can engage with the surface area at the distal end 402 of the bottle 400. In this manner, the bottle 400 together with the laminate seal element 403 can create an imperviously sealed unit that contains fluid medium.

By way of example, and not limitation, the laminate seal element 403 can be coupled to distal end 402 of the bottle 400 by any known methods, such as but not limited to heat sealing. The heat seal can provide a puncturable or rupturable seal, such that the laminate seal element 403 is removably coupled to the bottle 400. For example, the laminate seal element 403 can be peeled back or otherwise detachable from the bottle 400. Additionally or alternatively, the laminate seal element 403 can be detached, or unsealed, by any known methods, such as by being pierced with any suitable structure for engagement. By way of example, and not limitation, the laminate seal element 403 can be formed of a rupturable material. For example, and as discussed in further detail below, the laminate seal element 403 can be made of an aluminum foil or a polyethylene laminate material, or a polyester laminate material such as mylar or polyethylene terephthalate (PET) or a laminate structure constructed with a combination of the materials listed. As such, the laminate seal element 403 can be partially detached or unsealed from the bottle 400 by being pierced, thereby exposing an interior of the bottle 400.

Figure 6:
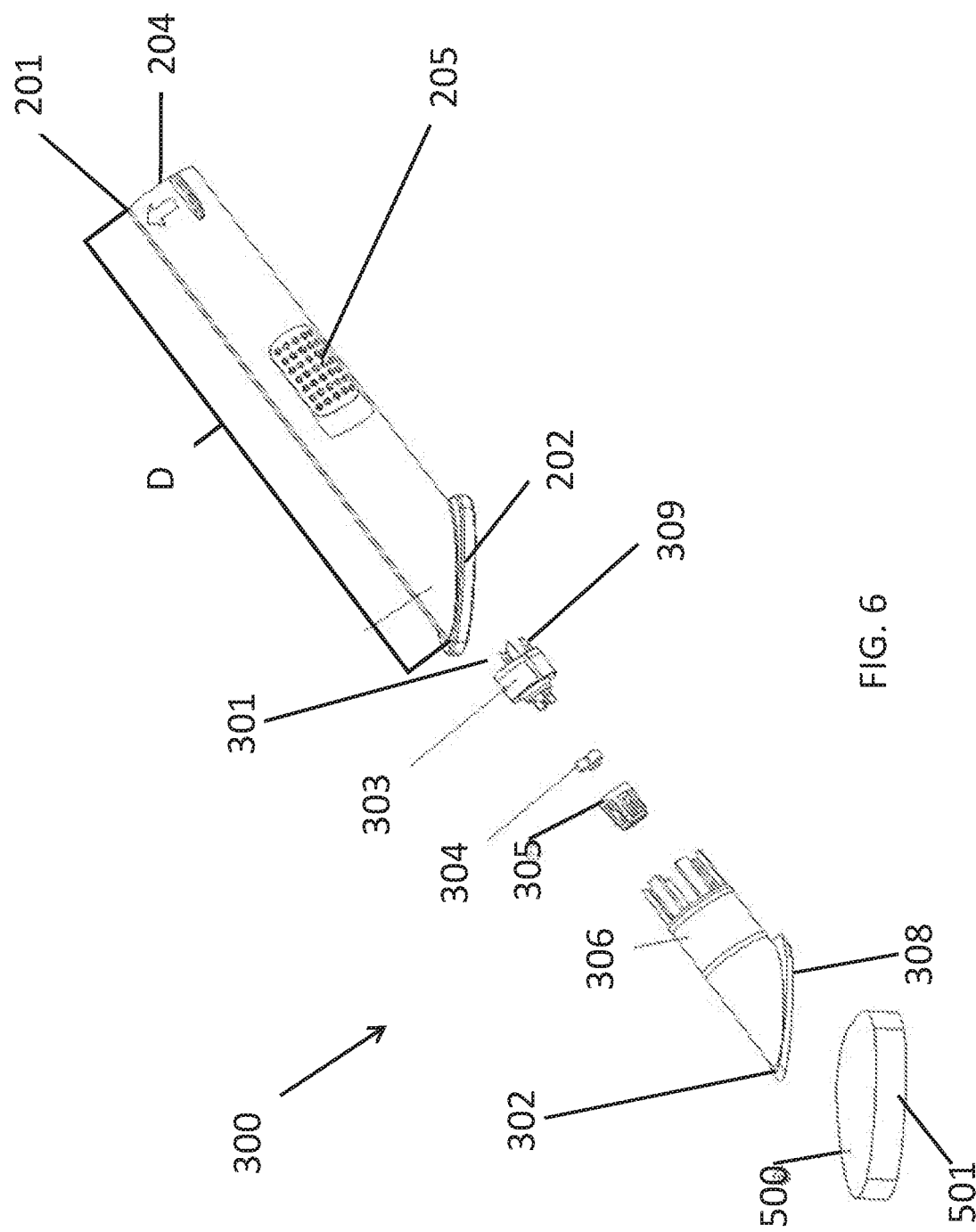
FIG. 6 is an exploded view of the housing, foam pad, basket and activation device assemblies of the fluid delivery device of FIG. 1, according to the disclosed subject matter.

FIG. 6 depicts an exploded view of another sub-assembly of the fluid delivery device 100 of FIGS. 1 and 2, comprising the housing 200, activation device 300, and foam pad 500. As embodied herein, the housing 200 can have a proximal end 201, a distal end 202, and a length D therebetween. The proximal end 201 of the housing 200 can define an aperture 204 such that the distal end 402 of the bottle 400 can be receivable within the aperture 204 of the housing 200. The distal end 202 of the housing 200 can further define an aperture to receive the activation device 300 and basket 305 and engage the foam pad 500, as further described herein.

Figure 7:
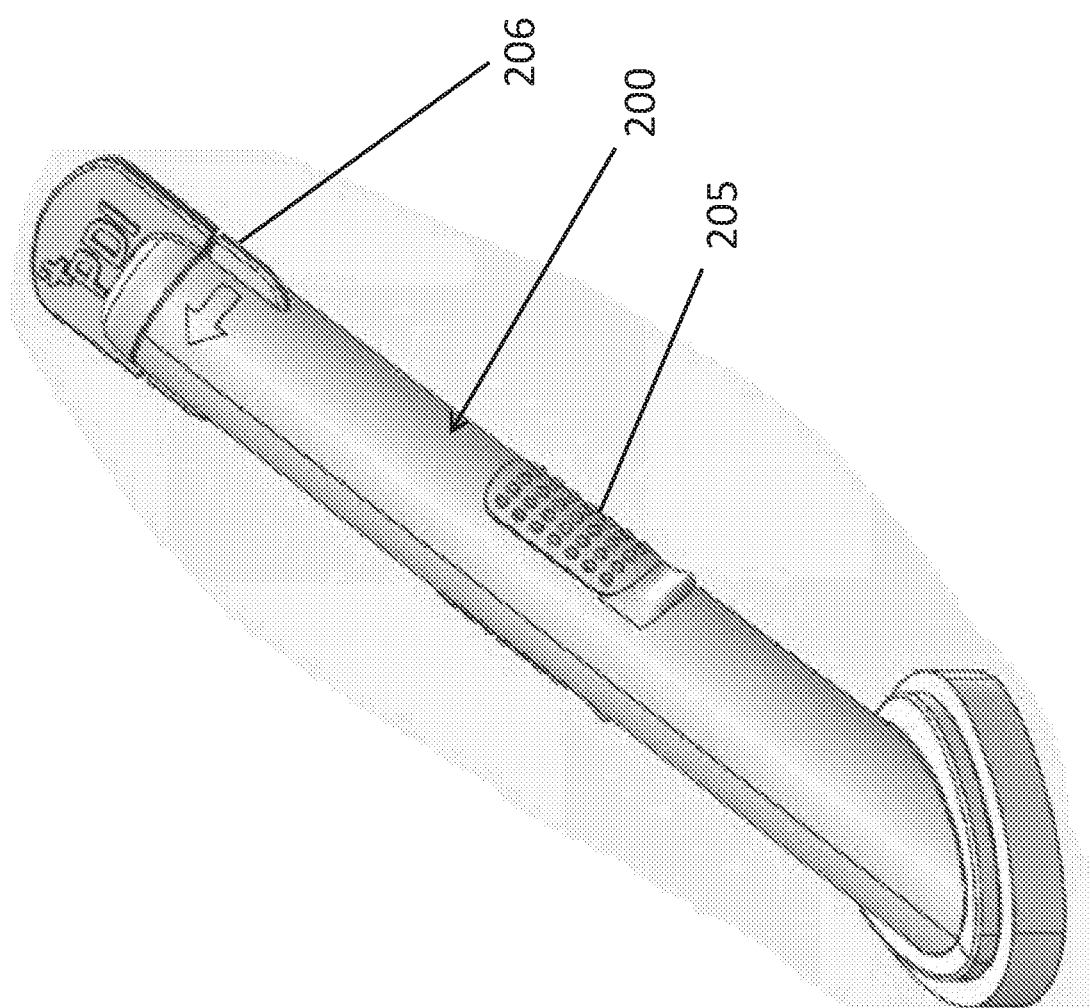
FIG. 7 is a perspective view of the fluid delivery device of FIG. 1 in a final position, according to the disclosed subject matter.

The housing 200 can further include a grip 205, as shown in FIG. 7. The grip 205 can be textured, as shown. Alternatively, the grip 205 can include indentations to complement a user's hand and fingers. The housing 200 can also include tabs 206 at the proximal end 201 thereof, for stabilization of the housing 200 when rotating the bottle 400 therein, as further discussed herein.

Figure 8:
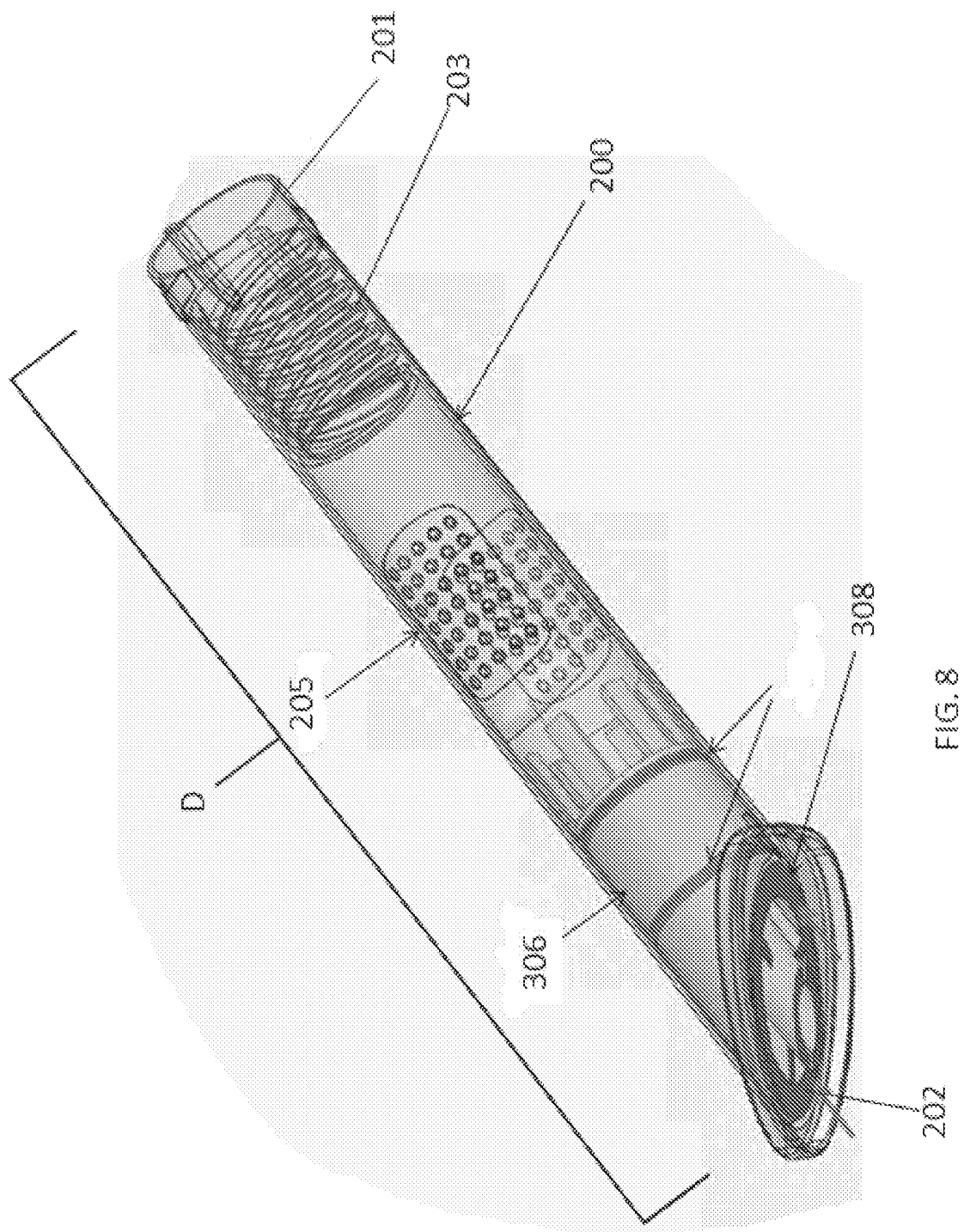
FIG. 8 is a transparent perspective view of the housing and activation device assemblies of the fluid delivery device of FIG. 1.

As embodied herein, and as shown in FIG. 8, the housing 200 can further include interior threads 203. Such interior threads 203 are disposed on an interior surface and interior sidewall of the housing 200. The interior threads 203 can be disposed proximate the proximal end 201 of the housing 200. The interior threads 203 can be disposed along a portion of the interior surface and sidewall of the housing 200 proximate the proximal end 201 of the housing 200. Alternatively, the interior threads 203 can be disposed about other portions along the interior surface and sidewall of the housing 200, including along a length D of the interior surface of the housing 200 to complement the threads of the bottle. Additionally, and for example and not limitation, the housing 200 and the interior threads 203 can be integrally formed from the same material.

As embodied herein, the interior threads 203 can be circumferentially disposed along the interior surface and sidewall of the housing 200. Alternatively, the interior threads 203 can be partially circumferentially disposed along the interior surface and sidewall of the housing 200. The interior threads 203 can be a bead projection, or alternatively, can define a flange. In addition to facilitating axial movement of the bottle 400 with respect to the housing 200, the interior threads 203 can also aid in stabilizing the bottle 400 within the housing 200. Thereby, the interior threads 203 can prevent transverse movement of the bottle 400 with respect to the housing 200.

The interior threads 203 of the housing 200 can be engageable with the exterior threads 406 of the bottle 400 to facilitate the axial movement of the bottle 400 with respect to the housing 200. For example, and not limitation, the interior threads 203 of the housing 200 can include threading that is complementary to the threading of the exterior threads 406 of the bottle. In such a configuration, when the bottle 400 is rotated relative to housing 200, the interior threads 203 of the housing 200 engage the exterior threads 406 of the bottle, thereby axially moving the bottle 400 into the housing 200 towards the foam pad 500.

As embodied herein, the fluid delivery device 100 can further include an activation device 300. As depicted in FIG. 1 and FIG. 2, the activation device 300 can be disposed within the housing 200. The activation device 300 can be disposed entirely within the housing 200, or can be disposed in part within a portion of the housing 200. The activation device 300 can have a proximal end 301 and a distal end 302. The proximal end 301 of the activation device 300 engages the laminate seal element 403 of the bottle 400 to dispense the fluid medium from the bottle 400. As described in further detail below, the dispensed fluid medium can then be channeled to the foam pad 500.

Figure 9:
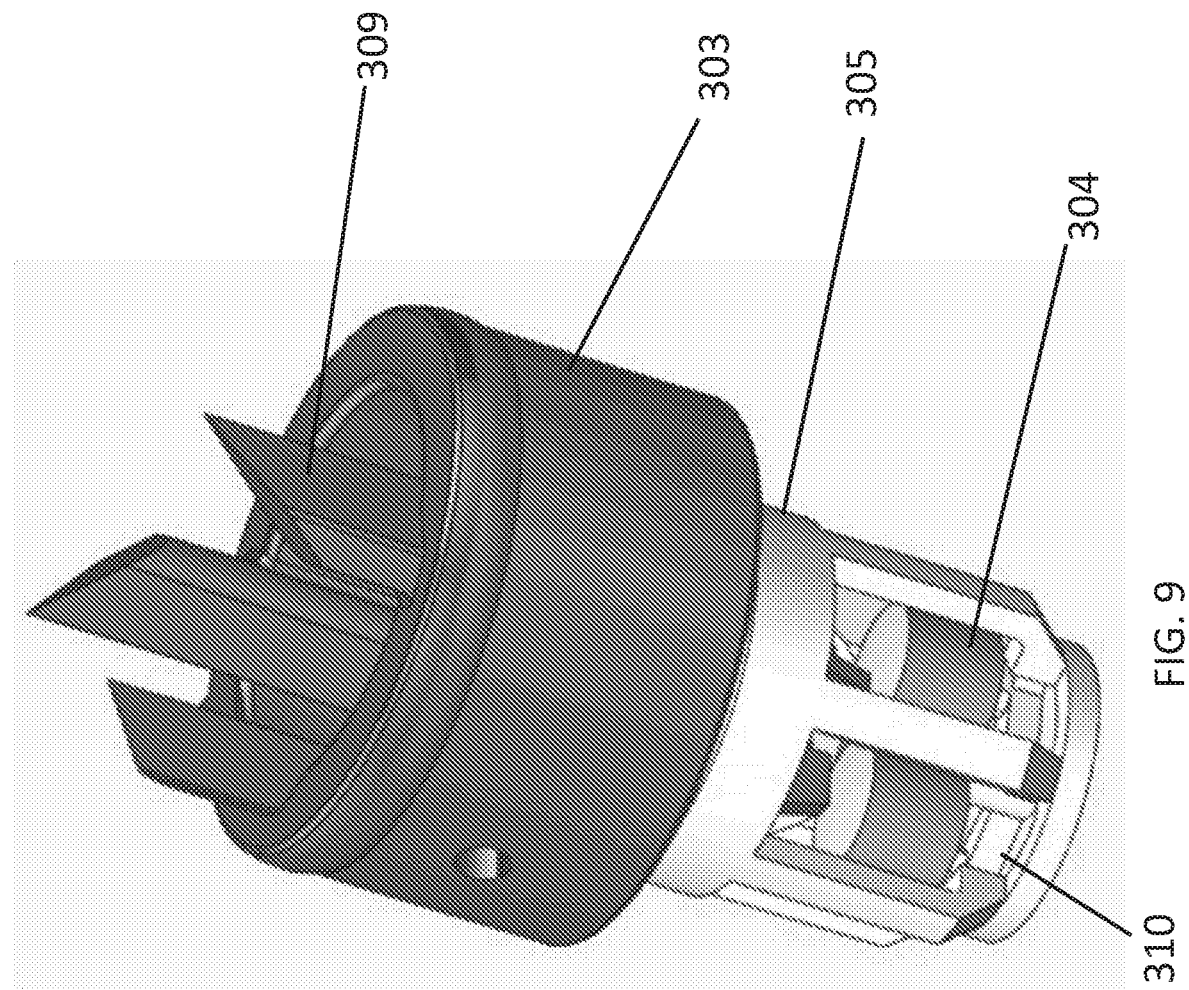
FIG. 9 is a perspective view of the cutter engaged with the basket containing least one dye tablet of the fluid delivery device of FIG. 1, according to the disclosed subject matter.
Figure 10:
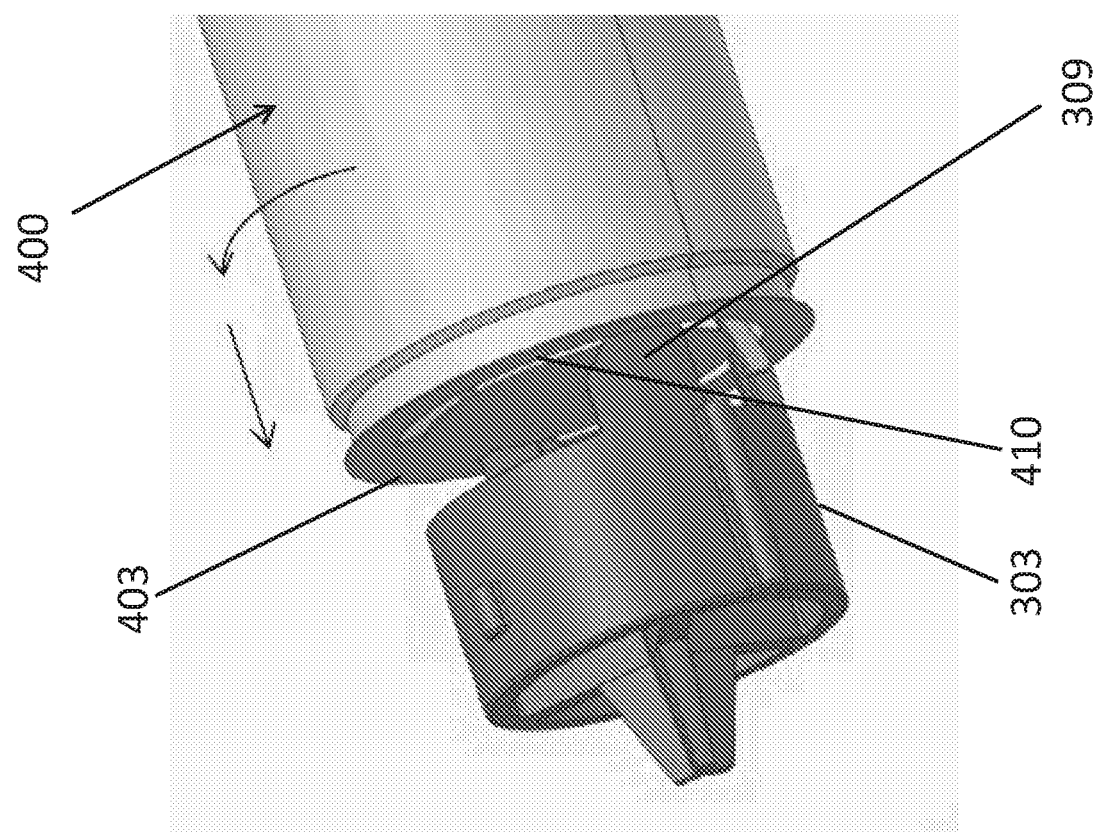
FIG. 10 is an enlarged perspective view of a portion of the fluid delivery device of FIG. 1 showing the cutter engaging the laminate seal element, according to the disclosed subject matter.

The activation device 300 can have any suitable dimension and configuration suitable to engage a laminate seal element 403. For example, and with reference to FIG. 6 and FIG. 9, the activation device 300 can comprise a cutter 303 disposed at a proximal end 301 of the activation device 300. By way of example and not limitation, the cutter 303 can comprise at least one piercing element 309, as depicted in FIG. 9. The cutter of FIG. 9 includes three (3) piercing elements 309 for purposes of example. Additionally, and as depicted in FIG. 10, a distal portion of the cutter 303 can extend within the basket 305 to engage the at least one dye tablet 304, thereby temporarily stabilizing the at least one dye tablet 304 within the basket 305.

The at least one piercing element 309 can have any dimension and configuration suitable to pierce a laminate seal element 403. Additionally, the piercing element 309 can be made of any material sufficiently hard enough to pierce a laminate seal element 403, such as a metal or plastic. In such embodiments and with reference to FIG. 10, upon engagement of the laminate seal element 403 with the activation device 300, the at least one piercing element 309 can create an arcuate shaped puncture 410 in the laminate seal element 403, thereby unsealing the laminate seal element 403 to allow for the fluid medium contents of the bottle 400 to dispense from the bottle 400. In such embodiments, the cutter 303 does not act as a plug.

Figure 11:
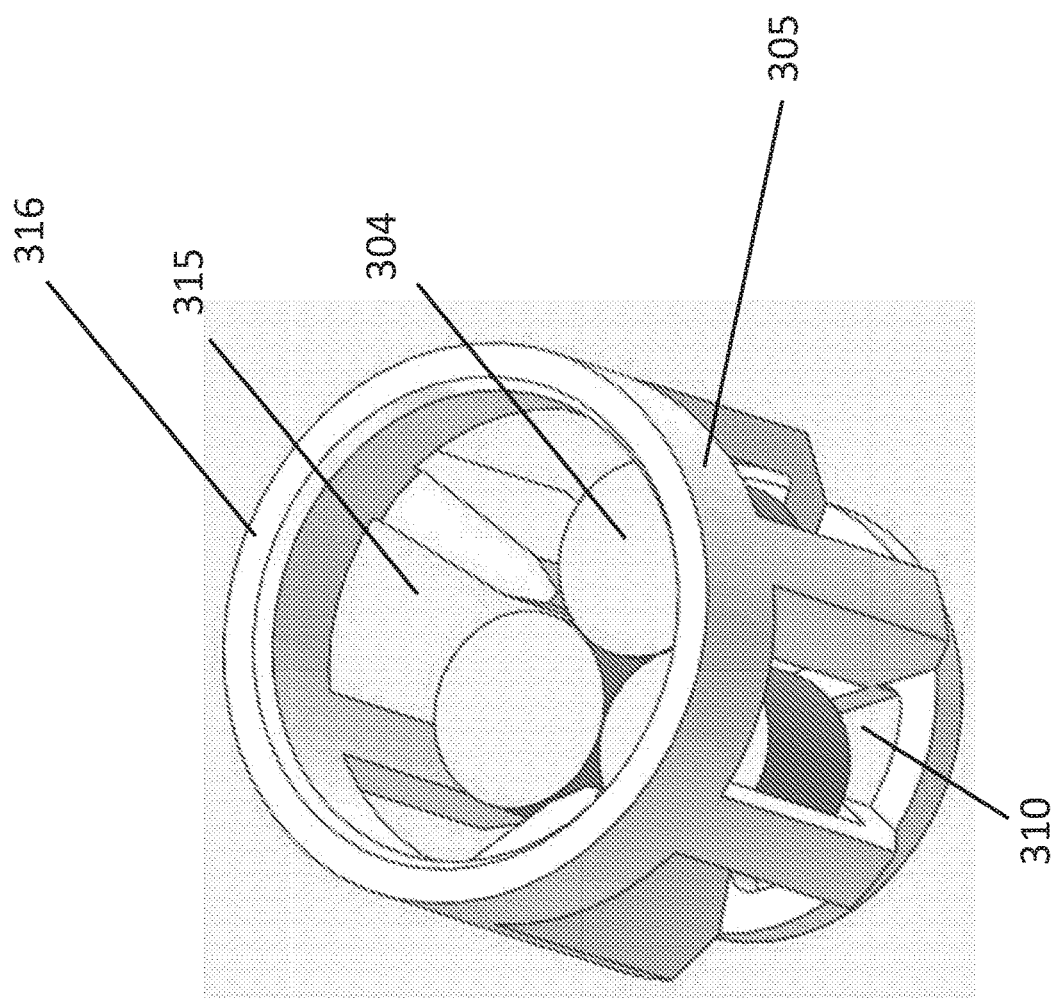
FIG. 11 is a perspective view of the basket and at least one dye tablet of the fluid delivery device of FIG. 1, according to the disclosed subject matter.

As embodied herein and as depicted in FIG. 11, the activation device 300 can further include a basket 305. The basket 305 can be disposed distal to and engaged with the cutter 303, as previously discussed above. As depicted in FIG. 11, the basket 305 of the activation device 300 can house the at least one dye tablet 304. In the embodiment of FIG. 11, the basket contains three tablets. The basket 305 can further include a plurality of recesses 310. The recesses 310 can include any suitable configuration such as a slit, window, or the like. The recesses 310 also are dimensioned such that the at least one dye tablet 304 can remain housed within the basket 305 in a non-disintegrated form. The basket 305 can have an open proximal end 315. The proximal end 315 of the basket 305 can define a recessed ledge 316 to receive the cutter 303 or other structure therein.

The pattern of the recesses 310 as depicted in the embodiment of FIG. 11 is an ordered pattern in which the recesses 310 are equally spaced from each other. However any other designs and configurations of recesses 310 are suitable for the purposes described above are further contemplated herein. The recesses 310 promote the delivery of the fluid medium to the top and sides of the at least one dye tablet 304. Further, the recesses 310 promote quick and even disintegration of at least one dye tablet 304 into the fluid medium, thereby creating the conditioned fluid, as further described herein.

As embodied herein the at least one dye tablet 304 can contain a dye of at least one color. When the at least one dye tablet 304 comes into contact with the fluid medium, the at least one dye tablet 304 can disintegrate within the fluid medium to form a conditioned fluid. As such, the color of the dye from the at least one dye tablet 304 is then imparted to the conditioned fluid. The color of the dye used to condition the fluid medium makes the conditioned fluid more visible on the skin.

The color of the dye in the at least one dye tablet 304 can be predetermined based upon the color of the skin of the patient to which the conditioned fluid will be applied. For example, the color of the dye in the dye tablet 304 can be varying shades of orange or teal, which is suitably visible when applied to a variety of skin colors. Further, the use of at least one dye tablet 304 to impart color in the fluid medium allows a more controlled delivery of color per mL of fluid medium in comparison with conventional devices. Additionally, the use of at least one dye tablet 304 to impart color on the fluid medium provides flexibility, in that at least one dye tablet 304 can be manufactured to contain the dye of any desired color, and can be manufactured in any size, shape, geometry or form to accommodate the functional requirements of the fluid delivery device (e.g., the size) and the dissolution and suspension requirements of the delivered fluid (e.g. the rate and percentage). Further, by separation of the dye tablet from the fluid medium, the fluid delivery device can include a longer shelf life when compared to conventional devices. For embodiments of the fluid delivery device 100 that do not desire a colored conditioned fluid, the basket 305 can be empty. Alternatively, the fluid delivery device 100 can be manufactured without such basket 305 and alternatively have the cutter 303 engage directly with the funnel 306, as discussed further herein.

For purposes of example, an orange dye tablet according to the disclosed embodiment can include any suitable ingredients, such as dyes (i.e., FD&C Red #40, D&C Yellow #19) and excipients and other ingredients (such as Natrosol, Polyplasdone XL, Ac-di-sol, Cabosil M-5 and Sodium Stearyl Fumerate, Hydroxyethyl cellulose, Crospovidone, Croscarmellose sodium, Fumed silica). The excipients can include Generally Recognized As Safe (GRAS) excipients as provided by the Food and Drug Administration (FDA). In one embodiment, the dye tablet has a weight of approximately 40 mg and an approximate diameter of 0.156 inch. This attribute can be infinitely variable depending on the rate and percentage of dye desired per unit volume (mL) of liquid delivered or dispensed.

Figure 12:
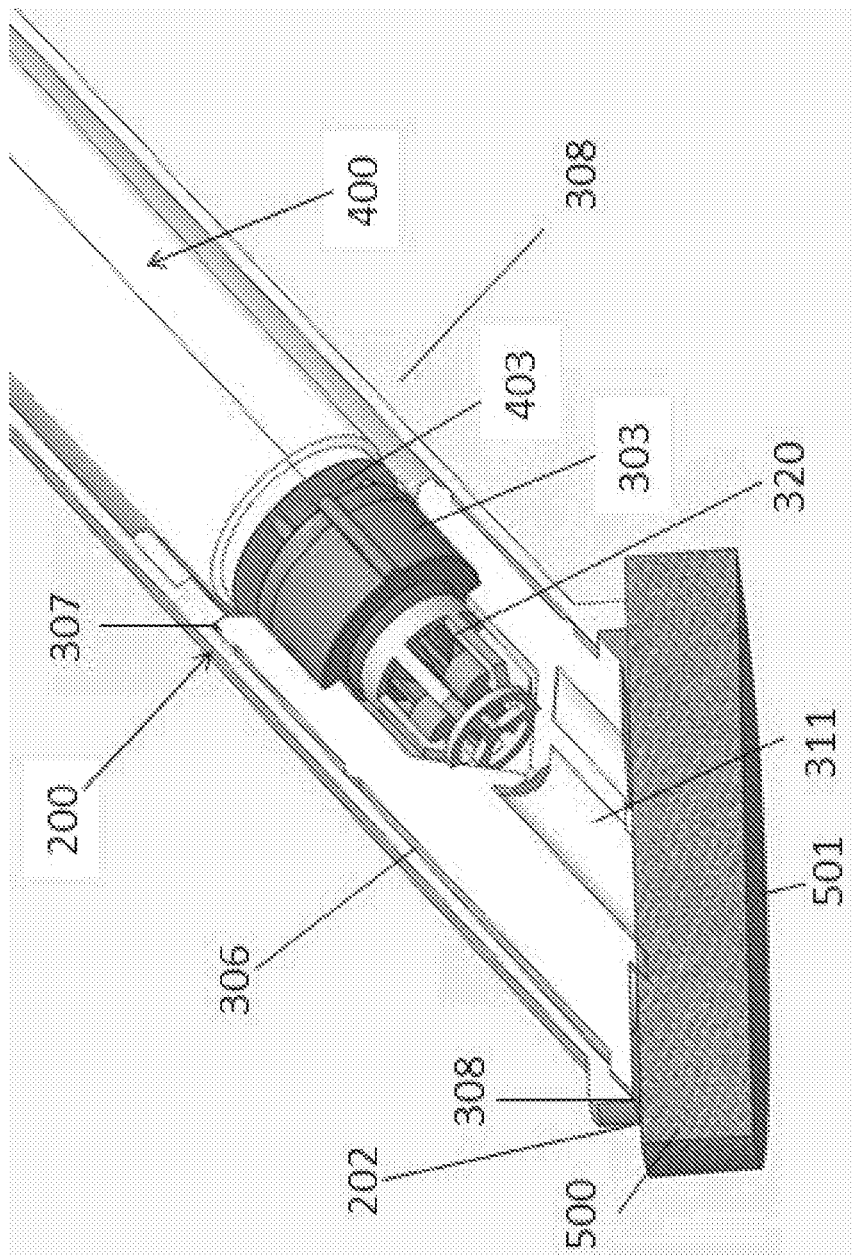
FIG. 12 is an enlarged perspective view of a portion of the fluid delivery device of FIG. 1 showing the housing, foam pad, and funnel.
Figure 13:
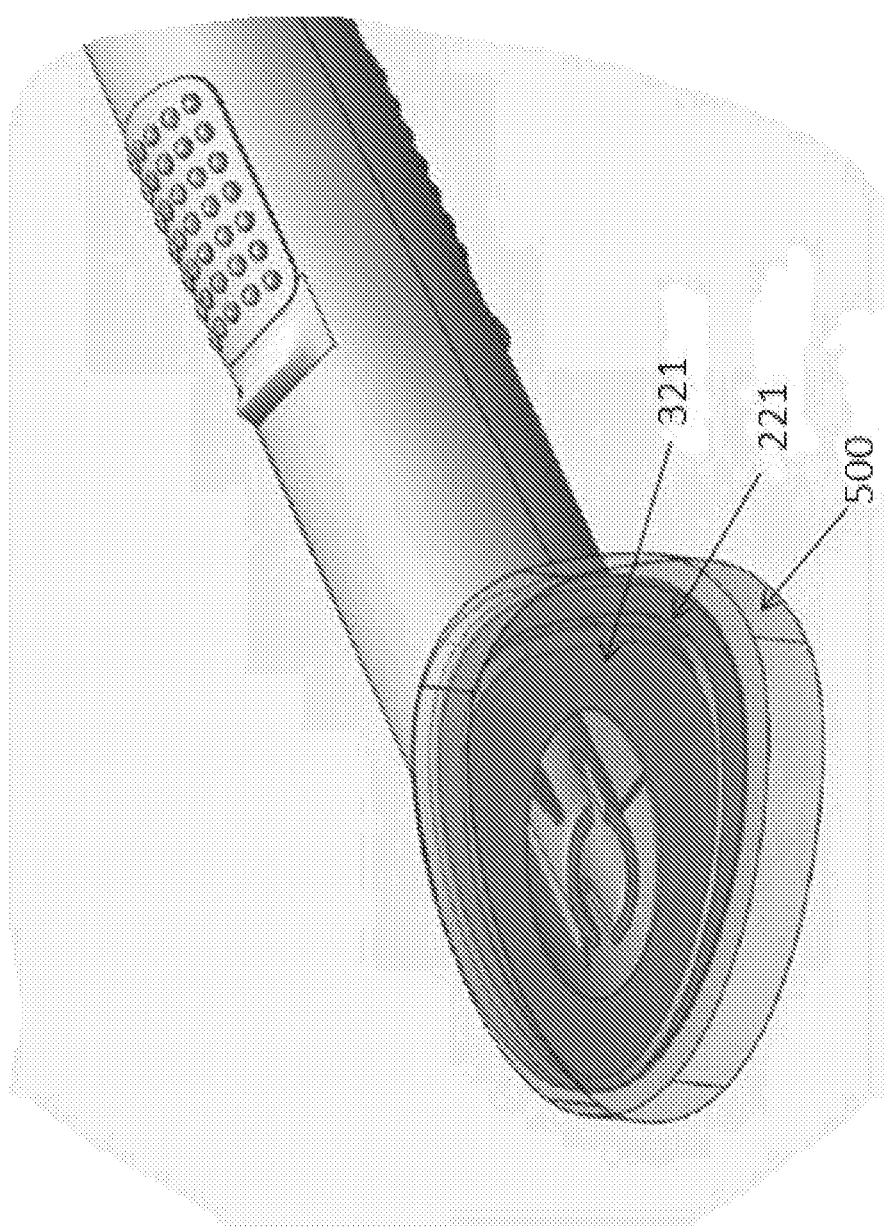
FIG. 13 is an enlarged cross sectional perspective view of an embodiment of the fluid delivery device of FIG. 2.

As embodied herein, and as depicted in FIGS. 12 and 13, the activation device 300 can further include a funnel 306 having a proximal end 307 and a distal end 308. The funnel 306 can be disposed distal to the cutter 303 and proximate the foam pad 500. The funnel 306 can include at least one funnel channel 311 configured to channel either the fluid medium dispensed from the bottle or the conditioned fluid to the foam pad 500. The basket 305 housing the at least one dye tablet 304 can be at least partially disposed within a mixing chamber 320 of the funnel 306. As the fluid medium is dispensed from the bottle 400 and flows distally towards the foam pad 500, the fluid medium flows into the proximal end 307 of the funnel 306 and continues beyond the cutter 303 to the mixing chamber 320. The fluid medium then flows over, around and through basket 305 within the mixing chamber 320 to allow interaction of the fluid medium with the at least one dye tablet 304. The fluid medium forms the conditioned fluid in the mixing chamber 320. The conditioned fluid flows towards the distal end 308 of the funnel 306, through the funnel channel 311 and is delivered to the foam pad 500. This configuration can facilitate an even distribution of the conditioned fluid into the foam pad 500 prior to and during delivery of the conditioned fluid to the patient's skin. As depicted in FIG. 8, the funnel is disposed within the housing. The distal end 308 of the funnel 306 can be proximate the distal end 202 of the housing 200.

As depicted in FIG. 12, the fluid delivery device 100 can further include a foam pad 500 coupled to at least the distal end 202 of the housing 200. The foam pad can also be coupled to the distal end 308 of the funnel 306. The foam pad 500 may be coupled to distal end 202 of housing 200 and/or funnel 306 by any known methods, such as but not limited to adhesive attachment, ultrasonic and heat welding. As depicted in FIG. 13, the distal end 308 of the funnel 306 can define a funnel lip 321 and the distal end 202 of housing 200 can define a housing lip 221 for engagement with the foam pad 500. The funnel lip 321 and the housing lip 221 can be co-planar, as shown in FIGS. 12 and 13. In such embodiments, the foam pad 500 engages both funnel lip 321 and the housing lip 221. Alternatively, the foam pad 500 may include a snap ring member (not shown) which is then coupled to the distal end 202 of the housing 200. As such, the foam pad can be detachable and can facilitate reuse of the housing upon removal of the foam pad 500, if desired.

As depicted the figures, the foam pad 500 can have a triangular shape, but any suitable shape is contemplated herein such as rectangular or square. In such embodiments where the foam pad 500 has a triangular shape, the triangular shape can facilitate deliverance of fluid medium to hard-to-reach areas, such as between toes and fingers, and between skin folds of the patient. The foam pad 500 can be any desired color or fabricated in such a way as to have a pattern or texture impressed upon the foam pad 500 during manufacturing, as described below.

Absorption of the conditioned fluid may be evident by visual observation of a color change of the foam pad 500. For example, the foam pad 500 may initially be a neutral color such as white or tan. The foam pad 500 can adopt the color of any fluid medium absorbed therein. For example, when the conditioned fluid is absorbed, the foam pad 500 can further adopt the color of the conditioned fluid. In other embodiments, where the fluid medium being absorbed by the foam pad 500 is clear, rather than colored, the foam pad 500 may become darker, indicating absorption of the fluid medium.

Once absorption by the foam pad 500 of the conditioned fluid or other fluid medium is evident by visual observation of the foam pad 500, the conditioned fluid or any other fluid medium may be applied to the surface of the patient's skin. The foam pad 500 can have an application surface 501 to facilitate the application to a patient. The foam pad 500 can release the fluid medium upon application of pressure to the foam pad 500, for example, upon pressure applied to the application surface 501 by the reciprocal force of the skin of a patient. Once the fluid medium or conditioned fluid is released from the bottle, the foam pad can be pressed against a treatment area of the patient to evenly distribute the solution throughout the foam pad and the foam pad can be further applied to the treatment area by using back-and-forth strokes, progressing from a center of the treatment area and to a periphery of the area. For treatment of an abdomen area, the application can be for at least 30 second and for treatment to a groin area, the application can be for at least 120 seconds.

The foam pad 500 can have any suitable thickness, such as for example and not limitation between about 0.18 inches to about 0.38 inches (0.38 cm to 0.97 cm) Such thickness, along with the interstitial spaces of the foam pad 500 and the material of the foam pad 500, can define a void volume of the foam pad 500. The void volume of the foam pad may be any suitable volume to provide sufficient absorption of a fluid for purposes disclosed herein, for example but not limitation, about 75 Pores per inch ("PPI") to about 125 PPI. Additionally, the foam pad 500 can have a smooth texture, or can alternatively have an abrasive texture to facilitate scrubbing of a patient's skin. The outer surface of the foam pad 500 can further define a design, such as a pattern of X's or V's (not shown).

As embodied herein, the foam pad 500 absorbs the fluid medium that is released from the bottle or the conditioned fluid. Once absorbed, the fluid medium is evenly distributed throughout the foam pad 500. The total amount of time beginning first with engagement of the laminate seal element 403 with the activation member 300, and ending with the absorption of the conditioned fluid within the foam pad 500 can vary based on a number of factors. Such factors can include the size of the fluid delivery device 100, the volume of fluid medium within the bottle 400, the dissolution time of the dye tablets, the nature of the fluid medium being absorbed, and the geometry of the foam pad 500. For example, the total time can include up to 30 seconds. Based on these factors dispensing time of the fully conditioned liquid to the foam pad may vary between 10 to 30 seconds.

Figure 14:
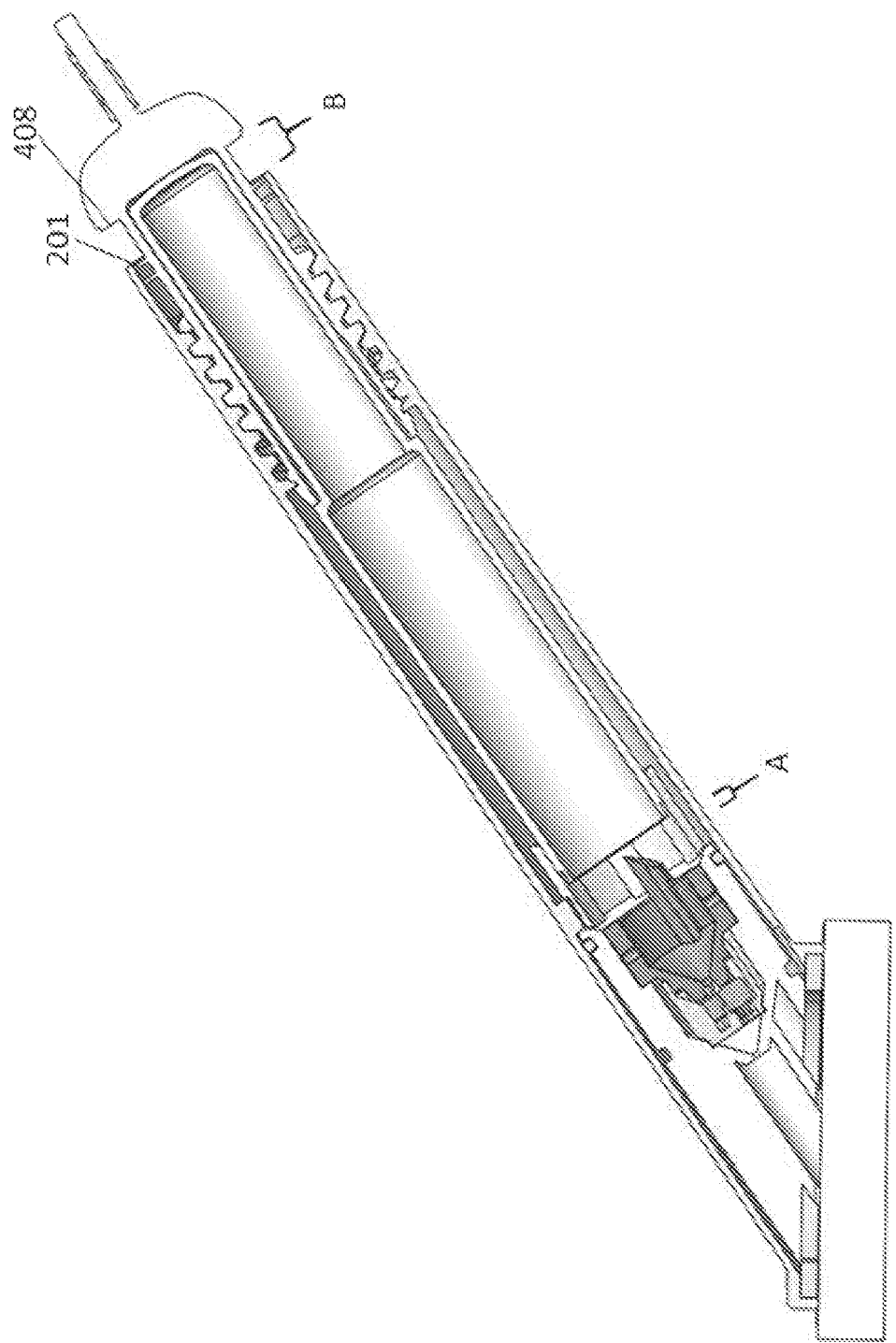
FIG. 14 is an cross sectional perspective view of an embodiment of the fluid delivery device of FIG. 1.

When the fluid delivery device 100 is assembled as a unit, as depicted in FIG. 1, the bottle 400 is received at least in part in the proximal end 201 of the housing 200. Further, when assembled, the laminate seal element 403 is disposed proximate the activation device 300 of the housing 200 and disposed a predetermined distance dimension A therefrom, as depicted in FIG. 14. The bottle 400 is axially movable with respect to the housing 200 at least the predetermined distance dimension A in order to engage the laminate seal element 403 with the activation device 300 to dispense the fluid medium from the bottle 400.

The predetermined distance dimension A can depend on the size and configuration of various components of the fluid delivery device 100. For example, in some embodiments, the predetermined distance dimension A may be approximately 0.12 inches (0.30 cm) along a longitudinal axis of the fluid delivery device 100. In the embodiment depicted in FIG. 1, the bottle 400 has not yet axially moved the predetermined distance dimension A with respect to the housing 200 (i.e. it is in an initial position). In the embodiment depicted in FIG. 2, the bottle 400 has axially moved at least the predetermined distance dimension A with respect to the housing 200 (i.e. it is in a final position).

As embodied herein, and as discussed above, the bottle 400 is rotatable with respect to the housing 200. Rotation of the bottle 400 can provide the axial movement the bottle 400 towards the distal end 202 of the housing 200, and as a result, the axial movement of the laminate seal element 403 towards the activation device 300. In some embodiments, the bottle can be rotated up to approximately 180° with respect to the housing 200 to impart axial movement of the bottle 400 at least the predetermined distance dimension A. In embodiments of the disclosed subject matter, further rotation of the bottle 400 with respect to the housing 200 will be prevented by a stop 408 once the bottle 400 has moved at least the predetermined distance dimension A, and the fluid delivery device will be in a final position, as discussed above.

Figure 15:
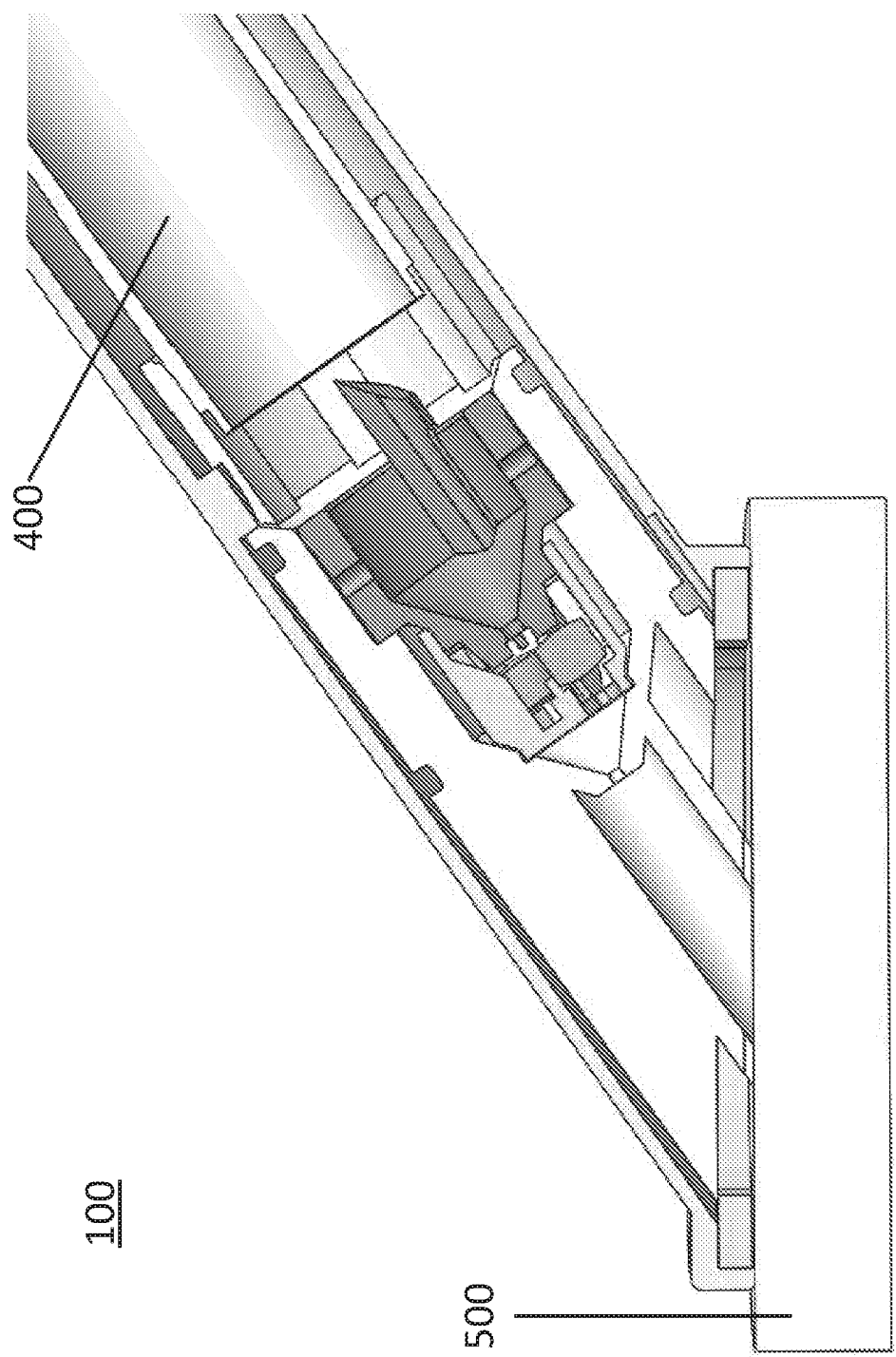
FIG. 15 is an enlarged cross sectional perspective view of an embodiment of the fluid delivery device of FIG. 2.

FIG. 14 shows the fluid delivery device 100 in an initial position, where the bottle 400 has not yet axially moved the predetermined distance dimension A with respect to the housing 200 (i.e. it is in an initial position). FIG. 14 also depicts a distance dimension B between the stop member 408 and the proximal end 201 of the housing 200. Once stop member 408 travels the distance B to contact the proximal end 201 of the housing 200, further axial movement of the bottle 400 within the housing 200 is prevented. The predetermined distance dimension A to permit first engagement of the activation device with the laminate seal element can be less than the distance dimension B. Alternatively, the predetermined distance dimension A can be the same as the distance dimension B. FIG. 15 shows the fluid delivery device 100 in a final position, where the bottle 400 has axially moved the predetermined distance dimension A with respect to the housing 200 (i.e. it is in a final position).

When the bottle 400 axially moves the predetermined distance dimension A with respect to the housing 200, the laminate seal element 403 engages the activation device 300, such as by piercing the laminate seal element 403 with the cutter, and the fluid medium is dispensed from the bottle 400. The force required to pierce the laminate seal element 403 of the bottle 400 with the activation device 300 can be minimal and can be equal to the rotational force exerted on the bottle 400 by a single finger of a user of the fluid delivery device. For purposes of example, the laminate seal element 403 can engage the activation device 300 after movement of the predetermined distance dimension of approximately 0.12 inches (0.30 cm) in order to unseal the laminate seal element 403 and to effectively cause the contents of the bottle 400 to be dispensed.

FIGS. 16A-19D depict further embodiments of the disclosed subject matter in which the fluid delivery device is axially movable from an initial position to a final position without rotational movement of the bottle therein. As such, in these embodiments, the fluid delivery device 100 can further be activated by a single-hand operation as further discussed herein.

FIG. 16A is a perspective view of a fluid delivery device 100 in an initial position and FIG. 16B is an exploded view of the bottle and activation device of the fluid delivery device of FIG. 16A. In this embodiment, the bottle 400 does not include circumferential exterior threads as provided in the previous embodiment. Rather, the bottle includes substantially even surface along a sidewall 407 thereof. As previously disclosed, the distal end 402 of the bottle includes a seal element 403 to seal the fluid medium therein. The distal end 402 of the bottle is coupled with a seal element 350 that secures the bottle within the housing to prevent transverse movement of the bottle 400 with respect to the housing 200 while permitting axial movement of the bottle within the housing 200 when activated. The seal element can be a tubular structure that defines a through-hole therein as shown. The seal element complements a shape of the proximal end 402 of the bottle for secure engagement.

As shown in FIGS. 16A and 16B, the proximal end 201 of the housing includes a first recess 210 and a second recess 220 whereas the bottle 400 includes a detent 415 disposed along the sidewall 407 at a proximal end 401 of the bottle. In the initial position, the detent 415 is disposed within the first recess 210 to prevent axial movement of the bottle within the housing as shown in FIG. 16A. As such, the bottle 400 is at least partially housed within the housing 200, but the closed proximal end 401 of the bottle is disposed exterior to the proximal end of the housing, as shown in FIG. 16A and as shown in the cross-sectional side view of FIG. 16C. In the initial position, the seal element 403 of the bottle remains intact and is disposed proximate the cutter 303 of the activation device 300, as shown in FIG. 16C.

The bottle 400 can transition from the initial position of FIGS. 16A and 16C to the final position of FIG. 16D upon applying a force F to the proximal end of the bottle 400. With application of suitable force F such as by a thumb, the detent 415 releases from the first recess 210 travels along the inner surface of the housing and is inserted within the second recess 220 to the final position. With the axial movement of the bottle 400 from the initial position to the final position, the seal element 403 is pierced by the cutter 303 of the activation device to release the fluid medium from the bottle 400. As depicted in the cross-sectional side view of FIG. 16D, the bottle has transitioned to the final position such that the seal element 403 has been pierced by the cutter 303. The detent 415 can have a cammed or tapered profile with angled surfaces 415A, 415B to facilitate an ease of transition from the first recess 210 to the second recess 220, as shown in FIGS. 16A and 16E. The fluid delivery device of FIGS. 16A-16E can otherwise function in a similar manner as the previous embodiment, such as to permit the fluid medium to engage with the at least one dye tablet to create a conditioned fluid as further discussed above.

Figure 17C:
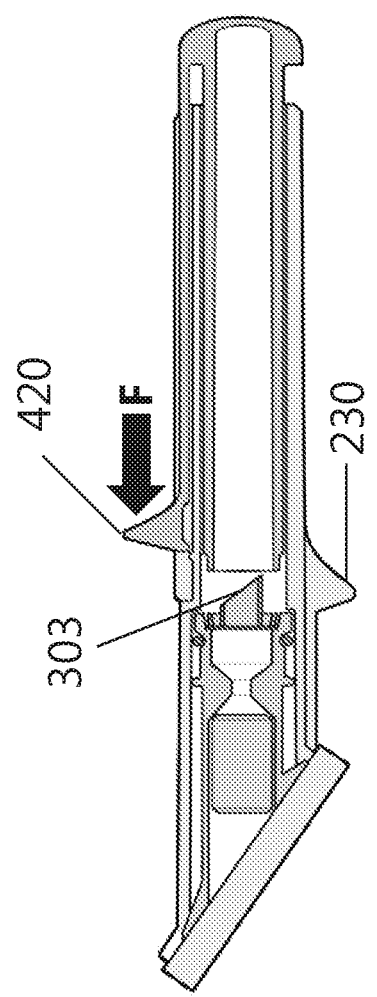
FIG. 17C is a side cross-sectional view of the fluid delivery device of FIG. 17A in the initial position.
Figure 17D:
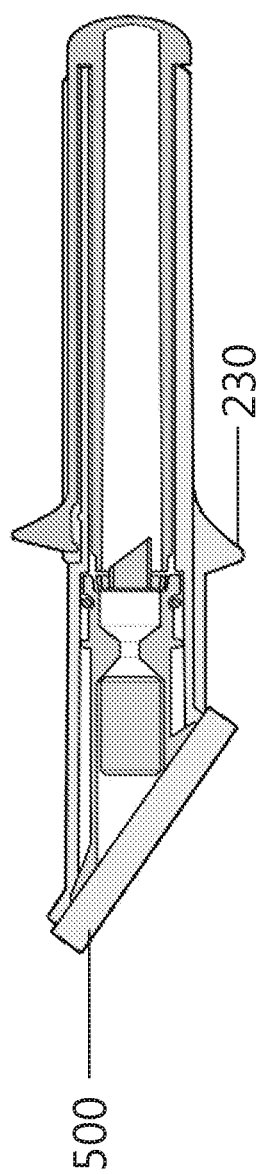
FIG. 17D is a side cross-sectional view of the fluid delivery device of FIG. 17C in the final position.

FIGS. 17A-17D depict another embodiment of the disclosed subject matter. FIG. 17A is a perspective view of a fluid delivery device in an initial position with FIG. 17C a cross-sectional side view thereof. FIG. 17B is an exploded view of the bottle and activation device of the fluid delivery device of FIG. 17A. FIG. 17D shows a side cross-sectional view of the final position of the fluid delivery device of FIG. 17A. In this embodiment, the housing includes a recessed longitudinal channel 225 and a finger rest structure 230 at a distal end portion thereof, at least as shown in FIG. 17A. The bottle includes a complementary raised longitudinal ridge 413 that is slideably received in the longitudinal channel 225 of the housing. The longitudinal ridge 413 includes a thumb protrusion 420 at a distal end thereof that can interface with a thumb of a user of the device 100. The device can be held in one hand with the fingers positioned along the bottom surface of the device and the thumb resting on the thumb rest 420. The finger rest structure 230 can be disposed between fingers such that any force exerted distally by the thumb onto the thumb rest to axially move the bottle with respect to the housing can be balanced by the grip of the device by the fingers between the finger rest structure 230. The axial distance the bottle moves with respect to the housing includes the predetermined distance dimension A as discussed further herein.

The bottle and the housing of FIGS. 17A-17D can further include a detent and recess structure (not shown), as further described above with respect to FIGS. 16A-16E. Alternatively, the housing of FIGS. 17A-17D can include other stop features, such as a circumferential ring and the like, to prevent movement of the bottle with respect to the housing in the initial position.

Similar to the previous embodiments, the bottle 400 is axially movable between the initial position of FIGS. 17A and 17C to the final position of FIG. 17D upon applying a force F to the thumb protrusion 420 in a direction towards the foam pad 500. With application of suitable force F such as by a thumb, any axial resistance from the stop features of the device is overcome to permit the bottle 400 to axially move to the final position. With the axial movement of the bottle 400 from the initial position to the final position, the seal element 403 is pierced by the cutter 303 of the activation device to release the fluid medium from the bottle 400 and otherwise operates in the same manner as previous embodiments.

As depicted in the cross-sectional side view of FIG. 17D, the bottle has transitioned to the final position by the distance dimension A, such that the seal element 403 has been pierced by the cutter 303. The proximal end of the bottle 401 can include a stop member such as a ledge 408 that prevents movement of the bottle with respect to the housing beyond the distance dimension A. The fluid delivery device of FIGS. 17A-17D can otherwise function in a similar manner as the previous embodiments, such as to permit the fluid medium to engage with the at least one dye tablet to create a conditioned fluid as further discussed above.

FIGS. 18A-18D depict another embodiment of the disclosed subject matter. FIG. 18A is a perspective view of a fluid delivery device in an initial position, and FIG. 18C is a side cross-sectional view thereof. FIG. 18B is an exploded view of the bottle and activation device of the fluid delivery device of FIG. 18A. FIG. 18D is a side cross-sectional view of the fluid delivery device of FIG. 18C in the final position. In this embodiment, the housing includes a lever 240 having a foot 245 and leg 247, as best shown in FIGS. 18A and 18C. The proximal end of the leg 247 defines a recess 249 that can engage with a hook 251 disposed along the sidewall of the housing 200, as shown. The lever 240 is pivotable with respect to the longitudinal length of the housing.

The bottle 400 defines a longitudinal recess 430 along at least a portion of a longitudinal length thereof and further includes an abutment surface 435 that abuts the leg 247 in the initial position, as shown in FIG. 18C. The device can be held in one hand with the fingers positioned along the bottom surface of the device and the thumb resting on the lever 240.

The bottle 400 can transition from the initial position of FIGS. 18A and 18C to the final position of FIG. 18D upon applying a force F to the lever 240. With application of suitable force F such as by a thumb, the foot 245 of the lever can engage with the abutment surface 435 to axially move the bottle in the axial direction towards the pad 500. With further force applied to the lever 240, the lever can further pivot towards the bottle 400 to permit the hook 251 to be received and locked within the recess 249 of the leg 247, as shown in FIG. 18D. With the axial movement of the bottle 400 from the initial position to the final position, the seal element 403 is pierced by the cutter 303 of the activation device to release the fluid medium from the bottle 400. In this embodiment, the housing includes an end cap 285 such that the bottle is contained within the housing in both the initial and final positions. However, as with the previous embodiments, this embodiment can further be utilized without an end cap. The fluid delivery device of FIGS. 18A-18D can otherwise function in a similar manner as the previous embodiments, such as to permit the fluid medium to engage with the at least one dye tablet to create a conditioned fluid as further discussed above.

FIGS. 19A-19D depict another embodiment of the disclosed subject matter. FIG. 19A is a perspective view of a fluid delivery device in an initial position and FIG. 19C is a top cross-sectional view thereof. FIG. 19B is an exploded view of the bottle and activation device of the fluid delivery device of FIG. 19A. FIG. 19D is a top cross-sectional view of the fluid delivery device of FIG. 19C in the final position. In this embodiment, the bottle further includes first and second wings 440 at a distal end thereof that are symmetrical about a longitudinal center axis of the device. The distal end of each wing 440 forms a curved segment 445 that engages with the housing 200, as further described herein. Each wing is movable inward towards the longitudinal center axis of the device between an initial position as shown in FIGS. 19A and 19C and a final position as shown in FIG. 19D. The arrows M indicate the direction of movement of the wings 440. Each wing 440 is coupled with a shaft of the bottle 400 at a juncture 447. Each wing includes a reduced thickness dimension at the juncture 447 to enable the wings to fold and collapse along the length of the bottle.

The housing 200 includes a flange 260 at a proximal end thereof that has a projection 265. The projection 265 interfaces with the curved segment 445 to couple the bottle with the housing. The curved segment 445 grips the projection 265 to allow the wings to grip the housing and facilitate axial movement of the bottle with respect to the housing.

The device can be held in one hand with the fingers positioned on the first wing 440 and the thumb positioned on the second wing 440 such that the device is contained within the palm of a user's hand. As such, the wings 440 can simultaneously collapse upon a force F exerted thereon by a user squeezing their fingers and thumb together. As the wings collapse, the bottle axially moves toward the pad 500. With the axial movement of the bottle 400 from the initial position to the final position, the seal element 403 is pierced by the cutter 303 of the activation device to release the fluid medium from the bottle 400. The fluid delivery device of FIGS. 19A-19D can otherwise function in a similar manner as the previous embodiments, such as to permit the fluid medium to engage with the at least one dye tablet to create a conditioned fluid as further discussed above.

The fluid medium contained within the bottle can be suitable for any medical application. For instance, the fluid medium contained within the bottle can be an antiseptic solution, and application of the solution to a portion of a body can kill microorganisms. In one embodiment, application of the antiseptic solution can kill microorganisms immediately and within approximately 10 minutes and further have a persistent effect for at least 7 hours. As such, the antiseptic solution can be used in preparing the body for surgery. In some embodiments, the antiseptic solution can comprise at least one of chlorhexidine gluconate (CHG), isopropyl alcohol, purified water, and mixtures thereof. In another embodiment, the antiseptic solution can comprise at least 3.15% w/v chlorhexidine gluconate and 70% v/v isopropyl alcohol (both ±10% w/v). The CHG can be designated as: 1,1'-hexamethylenebis [5-(p-chlorophenyl) biguanide] digluconate, and have the following chemical structure:

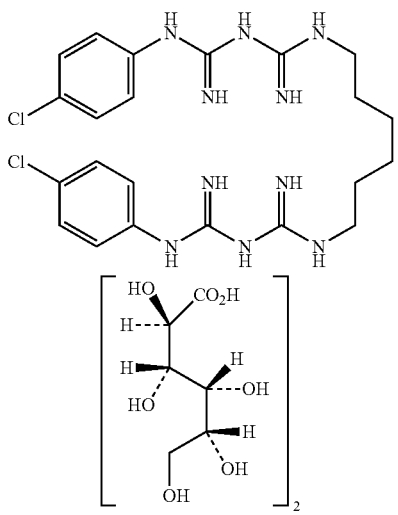

The fluid delivery device can be manufactured with any suitable material. In particular embodiments, the laminate seal element can comprise a commercial grade laminate structure manufactured of three discrete material layers, a top, middle, and bottom laminate layer, co-rolled and adhered to produce a unique laminate system. In such embodiments, the top, middle and bottom laminate layer materials can comprise Polyethylene terephthalate (PET), Aluminum, and Polyethylene (PE), respectively. Such laminate material can be produced by Amcor Flexibles (Shelbyville, Ky.) or Bemis Healthcare Packaging (Richmond, Va.).

In accordance the disclosed subject matter previously described, other components of the fluid delivery device can be made out of a plurality of suitable materials and can be formed by injection molding. For example, the handle, bottle, funnel, cutter and tablet basket can be molded of High Density Polyethylene (HDPE) or Polypropylene (PP). The interior of the bottle can be inert so as not to interact with solution therein. Alternatively, the bottle can be made of glass.

In accordance with the embodiments of the subject matter previously described, other the components of the foam pad can be made out of a plurality of suitable materials. For instance, the foam pad can be made of any suitable absorbent material. In another embodiment, the foam pad can be made out of any reticulated Polyester Polyurethane foam. A suitable foam can include products from FXI, Inc. (Fort Wayne, Ind.) or Foamtec International (Oceanside, Calif.).

The fluid delivery device can be disposed in a suitable primary sterile packaging. Further, the external components of the application can undergo ethylene oxide (EtO) sterilization, as practiced in the industry. An outer pouch with a breathable lid stock such as Tyvek from DuPont (Newark, Del.) to permit EtO in to ensure external sterility of the application while keeping out flora and other contaminants.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device and method of the disclosed subject matter without departing from the spirit or scope of the disclosed subject matter. Thus, it is intended that the disclosed subject matter include modifications and variations that are within the scope of the appended claims and their equivalents.

What is claimed is:

1. A fluid delivery device, comprising:
 a housing having a proximal end, a distal end, and a length therebetween;
 an activation device disposed within the housing;
 a bottle at least partially receivable in the proximal end of the housing, the bottle containing a fluid medium therein and sealed by a laminate seal element, wherein the laminate seal element is proximate the activation device and disposed a predetermined distance dimension therefrom; and
 a foam pad coupled to the distal end of the housing;
 wherein the bottle is axially movable with respect to the housing at least the predetermined distance dimension to engage the laminate seal element with the activation device to dispense the fluid medium from the bottle to the foam pad,
 wherein the activation device comprises a cutter disposed at a proximal end of the activation device, wherein the laminate seal element is unsealed by the cutter upon axial movement of the bottle the predetermined distance dimension,
 wherein the activation device further comprises at least one tablet, a basket disposed distal to the cutter, wherein the basket houses the at least one tablet, a funnel disposed distal to the cutter and proximate the foam pad, wherein the funnel is configured to channel the fluid medium dispensed from the bottle to the foam pad,
 wherein the fluid medium dispensed from the bottle engages the at least one dye tablet to form a conditioned fluid,
 wherein the at least one dye tablet is disintegrable within the fluid medium to form the conditioned fluid and a color from the at least one dye tablet is imparted to the conditioned fluid, and wherein the basket has a plurality of recesses to promote interaction of the at least one dye tablet with the fluid medium, and wherein the basket is receivable within the funnel.

2. The fluid delivery device of claim 1, wherein the cutter comprises at least one piercing element.

3. The fluid delivery device of claim 1, wherein the activation device comprises a monolithic structure.

4. The fluid delivery device of claim 1, wherein the fluid medium is absorbable by the foam pad.

5. The fluid delivery device of claim 4, wherein the foam pad releases the fluid medium upon application of pressure to the foam pad.

6. The fluid delivery device of claim 1, wherein the proximal end of the housing defines an aperture and the bottle is at least partially receivable within the aperture of the housing.

7. The fluid delivery device of claim 1, wherein the bottle is rotatable with respect to the housing.

8. The fluid delivery device of claim 7, wherein the housing further including interior threads at the proximal end thereof and the bottle further including exterior threads at a distal end thereof, wherein the interior threads of the housing are engageable with the exterior threads of the bottle to axially translate the bottle with respect to the housing.

9. The fluid delivery device of claim 8, wherein the bottle includes a handle at a proximal end thereof, wherein the bottle is rotatable by a movement of the handle to axially translate the bottle with respect to said housing.

10. The fluid delivery device of claim 9, wherein the handle and the bottle comprise a monolithic structure.

11. The fluid delivery device of claim 1, wherein a material of the laminate seal element comprises at least one of aluminum, plastic, or a combination thereof.

12. The fluid delivery device of claim 1, wherein the fluid medium comprises an antiseptic solution having at least one of chlorhexidine gluconate, isopropyl alcohol, and mixtures thereof.

13. The fluid delivery device of claim 1, wherein a volume of the bottle comprises at least 5 mL of the fluid medium.

14. The fluid delivery device of claim 1, wherein the foam pad has a triangular shape.

15. The fluid delivery device of claim 1, wherein the fluid delivery device includes an initial position with the laminate seal element uncompromised and a final position with the laminate seal element unsealed by the cutter, wherein the fluid delivery device is transitionable from the initial position to the final position upon axial movement of the bottle with respect to the housing.

16. A method of using a fluid delivery device, comprising:
providing a fluid delivery device including
 a housing having a proximal end, a distal end, and a length therebetween,
 an activation device disposed within the housing,
 a bottle at least partially receivable in the proximal end of the housing, the bottle containing a fluid medium therein and sealed by a laminate seal element,
  wherein the laminate seal element is proximate the activation device and disposed a predetermined distance dimension therefrom, and
 a foam pad coupled to a distal end of the housing;
  wherein the activation device comprises a cutter disposed at a proximal end of the activation device, wherein the laminate seal element is unsealed by the cutter upon axial movement of the bottle the predetermined distance dimension,
  wherein the activation device further comprises at least one tablet, a basket disposed distal to the cutter, wherein the basket houses the at least one tablet, a funnel disposed distal to the cutter and proximate the foam pad, wherein the funnel is configured to channel the fluid medium dispensed from the bottle to the foam pad,
  wherein the fluid medium dispensed from the bottle engages the at least one dye tablet to form a conditioned fluid,
  wherein the at least one dye tablet is disintegrable within the fluid medium to form the conditioned fluid and a color from the at least one dye tablet is imparted to the conditioned fluid, and
  wherein the basket has a plurality of recesses to promote interaction of the at least one dye tablet with the fluid medium, and wherein the basket is receivable within the funnel;
rotating the bottle within the housing to axially move the laminate seal element at least the predetermined distance dimension with respect to the housing; and
engaging the laminate seal element with the activation device to dispense the fluid medium from the bottle to the foam pad.

17. The method of claim 16, wherein the fluid medium interacts with the at least one dye tablet to create a conditional fluid.

* * * * *